US011325935B2

(12) United States Patent
Kameyama et al.

(10) Patent No.: US 11,325,935 B2
(45) Date of Patent: May 10, 2022

(54) METHOD FOR LIBERATING SUGAR CHAIN FROM GLYCOPROTEIN

(71) Applicants: NATIONAL INSTITUTE OF ADVANCED INDUSTRIAL SCIENCE AND TECHNOLOGY, Tokyo (JP); SUMITOMO BAKELITE CO., LTD., Tokyo (JP)

(72) Inventors: Akihiko Kameyama, Tsukuba (JP); Masaaki Toyoda, Tokyo (JP); Midori Sakaguchi, Tokyo (JP)

(73) Assignees: NATIONAL INSTITUTE OF ADVANCED INDUSTRIAL SCIENCE AND TECHNOLOGY, Tokyo (JP); SUMITOMO BAKELITE CO., LTD., Tokyo (JP)

( * ) Notice: Subject to any disclaimer, the term of this patent is extended or adjusted under 35 U.S.C. 154(b) by 0 days.

(21) Appl. No.: 16/335,939

(22) PCT Filed: Sep. 26, 2017

(86) PCT No.: PCT/JP2017/034717
§ 371 (c)(1),
(2) Date: Mar. 22, 2019

(87) PCT Pub. No.: WO2018/062167
PCT Pub. Date: Apr. 5, 2018

(65) Prior Publication Data
US 2019/0309003 A1   Oct. 10, 2019

(30) Foreign Application Priority Data
Sep. 27, 2016   (JP) .............................. JP2016-187961

(51) Int. Cl.
*C07H 1/00*   (2006.01)
*C07H 5/06*   (2006.01)
(Continued)

(52) U.S. Cl.
CPC ................. *C07H 1/00* (2013.01); *C07H 1/08* (2013.01); *C07H 5/06* (2013.01); *C08B 37/00* (2013.01);
(Continued)

(58) Field of Classification Search
CPC ............... C07H 1/00; C07H 1/08; C07H 5/06
See application file for complete search history.

(56) References Cited

U.S. PATENT DOCUMENTS 5,831,077 A *  11/1998  Redmond ............... C07K 1/128
                                                    536/55.3
2004/0039192 A1 *  2/2004  Packer .................... C07H 1/08
                                                    536/123
(Continued)

FOREIGN PATENT DOCUMENTS

GB       2 452 259 A     3/2009
JP       3-228000 A     10/1991
(Continued)

OTHER PUBLICATIONS

Highly Efficient Release of Glycopeptides from Hydrazide Beads by Hydroxylamine Assisted PNGase F Deglycosylation for N-Hlycoproteome Analysis Huang et al Anal. Chem. 2015, 87, 10199 (Year: 2015).*
(Continued)

*Primary Examiner* — Brian R Gordon
*Assistant Examiner* — Dwan A Gerido
(74) *Attorney, Agent, or Firm* — WHDA, LLP

(57) ABSTRACT

Provided is a method for liberating sugar chains from a glycoprotein, including: a step of brining a reaction solution which contains hydroxylamines (a) and a basic reagent (b) into contact with the glycoprotein to obtain a mixed solution of sugar chains liberated from the glycoprotein and the reaction solution.

11 Claims, 7 Drawing Sheets

(51) Int. Cl.
G01N 33/58 (2006.01)
C07H 1/08 (2006.01)
G01N 33/50 (2006.01)
C08B 37/00 (2006.01)

(52) U.S. Cl.
CPC ............ *G01N 33/50* (2013.01); *G01N 33/582* (2013.01); *G01N 2400/00* (2013.01)

(56) References Cited

U.S. PATENT DOCUMENTS

| | | |
|---|---|---|
| 2006/0188996 A1 | 8/2006 | Nishimura et al. |
| 2006/0211849 A1 | 9/2006 | Kakehi |
| 2009/0057549 A1* | 3/2009 | Kimura ............... C12Q 1/34 250/282 |
| 2011/0275108 A1 | 11/2011 | Nishimura et al. |

FOREIGN PATENT DOCUMENTS

| | | |
|---|---|---|
| JP | 2005-291958 A | 10/2005 |
| JP | 2007-45889 A | 2/2007 |
| JP | 4283272 B2 | 6/2009 |
| JP | 2009156587 * | 7/2009 |
| JP | 2012-189439 A | 10/2012 |
| JP | 2015-107969 A | 6/2015 |
| JP | 2016-220675 A | 12/2016 |
| JP | 2017-19994 A | 1/2017 |
| KR | 2000-0048051 A | 7/2000 |
| KR | 10-2013-0079151 A | 7/2013 |
| WO | 99/11819 A1 | 3/1999 |
| WO | 00/34312 A1 | 6/2000 |
| WO | 2004/077048 A1 | 9/2004 |

OTHER PUBLICATIONS

On the susceptibility to alkali and to hydroxylamine of the predominant carbohydrate peptide linkage in ovine submaxillary gland glycoprotein E.R.B. Graham, W.H. Murphy, A. Gottschalk Biochim. Bioophys. Acta 74 (1963) 222-238 (Year: 1963).*
International Search Report dated Dec. 19, 2017, issued in counterpart application No. PCT/JP2017/034717, w/English translation (5 pages).
Kameyama et al., "Chemically rapid glycan liberation method for evaluating oligosaccharide heterogeneity of antibody therapeutics", Abstracts of the 36th Annual Meeting of Japanese Society of Carbohydrate Research, Jul. 10, 2017, p. 70 1B-01 (2 pages).
Office Action dated Oct. 29, 2019, issued in Japanese Patent Application No. 2018-542590, with English machine translation.
"2.2 organic sample, Research Chemistry, 20-1", The Chemical Society of Japan, 2007, vol. 5, pp. 51-69, cited in Japanese Office Action dated Oct. 29, 2019.
Graham, E. R. B. et al., "Studies of Mucoproteins IX. On the susceptibility to alkali and to hydroxylamine of the predominant carbohydrate-peptide linkage in ovine-submaxillary-gland glycoprotein", Biochimica Et Biophysica ACTA, Elsevier, NL, vol. 74., Jan. 1, 1963, pp. 222-238; Cited in EPOA dated May 4, 2020.

* cited by examiner

METHOD FOR LIBERATING SUGAR CHAIN FROM GLYCOPROTEIN

TECHNICAL FIELD

The present invention relates to a method for liberating sugar chains from a glycoprotein. Priority is claimed on Japanese Patent Application No. 2016-187961, filed on Sep. 27, 2016, the content of which is incorporated herein by reference.

BACKGROUND ART

Sugar chains are bound to many proteins, including biopharmaceuticals such as antibody drugs. In the biopharmaceuticals, it is suggested that sugar chains affect not only the activity of the pharmaceuticals thereof but also the antigenicity or kinetics thereof. Therefore, analysis of sugar chains has become an important issue in the development of the biopharmaceuticals. Further, sugar chains of glycoproteins can be used as disease-related biomarkers. In order to find sugar chains which can be used as markers, it is necessary to analyze sugar chains of glycoproteins contained in biological samples of polyspecimens.

Further, "Guidance for Analyzing Quality of Antibody Drugs" of the Ministry of Health, Labour and Welfare describes that, since it is considered that the dose of antibody drugs is large and the content of non-human type sugar chains may be higher than that of the related art depending on the cells used for production, the proportion thereof needs to be clarified and the impact on safety needs to be considered. Therefore, in the sugar chain analysis, attention needs to be paid not to overlook sugar chain structures that are not present in humans, specifically, N-glycolylneuraminic acid, Gal$\alpha$1-3Gal structure, and the like.

As a method for analyzing sugar chains, a method for liberating sugar chains from a glycoprotein, performing a post-treatment such as desalting or deproteinization, and analyzing the sugar chains using a mass spectrometer or a method for imparting fluorescent labeling to liberated sugar chains and analyzing the sugar chain using high performance liquid chromatography provided with a fluorescent detector, capillary electrophoresis, or a combination of these has been typically used. In both cases, the first stage is to liberate sugar chains from a glycoprotein. The binding between sugar chains and proteins is divided into N-binding sugar chains in which N-acetylglucosamine is linked to an amino group of an asparagine residue of a protein through an N-glycosidic bond and O-binding sugar chains in which N-acetylgalactosamine is linked to a hydroxyl group of serine and a threonine residue through an O-glycosidic bond. In order to liberate sugar chains from proteins, respectively suitable methods are used.

In order to liberate N-binding sugar chains, the sugar chains can be liberated using enzymes such as PNGaseF or Glycopeptidase A, but it is necessary to use enzymes properly according to the biological species to be analyzed due to the fact that the substrate specificity of each enzyme varies. Further, pre-treatments such as denaturation of proteins in advance or decomposition of proteins with protease are typically performed for the purpose of improving the sensitivity of the enzyme reaction.

In addition, methods of liberating sugar chains by causing chemical reactions without using enzymes may be employed. For example, PTL 1 discloses a hydrazine decomposition method for dissolving glycoproteins, which have been sufficiently dried, in anhydrous hydrazine and performing a heat treatment at 100° C. for 10 hours or longer, and this method has been mainly used as a method for liberating N type sugar chains. The anhydrous hydrazine is distilled off under reduced pressure after the reaction, and acetylation is further carried out using sodium hydrogen carbonate and acetic anhydride. Since hydrazine also decomposes an N-acetyl group and an N-glycolyl group bound to sugar chain so that these groups are converted to amino groups, an operation of acetylation is carried out in order to return the original state. Therefore, even in a case where other acyl groups such as an N-glycolyl group are originally bound to sugar chains, these are all analyzed as N-acetyl bodies.

For example, in PTL 2, liberation of sugar chains using a hydrazine-hydrate has been also reported. This method is used in a case of treating a large amount of glycoproteins because a hydrazine-hydrate is relatively easily handled and inexpensive compared to hydrazine. However, this method also requires the post-treatments such as hydrazine distillation and re-acetylation after the reaction by performing the same steps as in the hydrazine decomposition method.

Enzymes with practicality which can be used for liberating O-binding sugar chains have not been found. Consequently, liberation has been carried out only using chemical reactions. A method for β-eliminating sugar chains in a strong alkali aqueous solution has been widely used as the chemical reaction for carrying out liberation. However, since liberated sugar chains are immediately decomposed in the presence of an alkali, a method for immediately reducing liberated sugar chains to alditol by carrying out a reaction in the coexistence of sodium borohydride has been typically used.

Fluorescent labeling cannot be imparted to the liberated alditol because an aldehyde group serving as a functional group on a sugar chain side for imparting fluorescent labeling is reduced and changed to an alcohol. Therefore, the analysis using a mass spectrometer is typically performed by methylating (complete methylation) all hydroxyl groups in alditol.

PTL 3 discloses a system of reacting an alkali solution with a sample solution for a short period of time while allowing the solutions to flow in a flow path and immediately carrying out a neutralization treatment in order to obtain O-binding sugar chains in a state in which an aldehyde group is preserved in β-elimination using a strong alkali.

The above-described hydrazine decomposition method has been known as another method for chemically liberating O-binding sugar chains in a state in which an aldehyde group is preserved. After the reaction, hydrazine distillation and re-acetylation are performed, and fluorescent labeling is imparted. Thereafter, analysis is performed using HPLC or the like.

Since the liberation of O-binding sugar chains according to the hydrazine decomposition method is accompanied by decomposition of sugar chains, an attempt of adding an additive to the reaction system for the purpose of minimizing the decomposition has been reported. Similarly, since β-elimination using a strong alkali is also accompanied by decomposition, a β-elimination method using a weak salt group in place of a strong alkali has been examined, and a method of using concentrated ammonia water, a method of using ammonium carbamate (PTL 4), and the like have been reported.

CITATION LIST

Patent Literature

[PTL 1] Japanese Unexamined Patent Application, First Publication No. H03-228000
[PTL 2] Japanese Unexamined Patent Application, First Publication No. 2007-45889
[PTL 3] Japanese Patent No. 4283272
[PTL 4] Japanese Unexamined Patent Application, First Publication No. 2015-107969

SUMMARY OF INVENTION

Technical Problem

Monitoring and controlling non-uniformity of sugar chains in biopharmaceuticals from the drug discovery stage to the production of drugs through development stage have become important issues in production of high-quality biopharmaceuticals. It is necessary to promptly analyze sugar chains at each stage of development constantly instead of analyzing sugar chains only for the purpose of quality control of products as has been done so far in the related art. Further, it is necessary to promptly analyze polyspecimen samples in the analysis of sugar chains in order to search pathologic condition markers related to various diseases. Further, the cost becomes an extremely heavy burden at the time of analysis of polyspecimens.

The first stage is to liberate sugar chains from proteins in order to analyze sugar chain as described above. However, in the related art, liberation of sugar chains including the pre-treatment takes a long time. For example, in a case where sugar chains are liberated using enzymes, since proteins are treated using a reducing agent such as dithiothreitol in advance, treated using an alkylating agent such as iodoacetamide so as to be denatured, decomposed to peptides using protease such as trypsin, and allowed to react with a sugar chain-liberating enzyme so that sugar chains are liberated, it is impossible to analyze sugar chains on the day when samples have been recovered in the production site of pharmaceuticals.

Further, PNGaseF and glycopeptidase A which are enzymes that liberate sugar chains are extremely expensive, and thus it is necessary to bear cost burden in order to analyze polyspecimens.

Further, since the hydrazine decomposition method requires perfect anhydrous conditions, the yield is drastically decreased in a case where even a small amount of water is mixed into the reaction system. Therefore, the reaction needs to proceed after the sample is sufficiently dried under reduced pressure. Further, the reaction time is 10 hours or longer, and it takes at least two days to complete all steps including distillation of hydrazine and re-acetylation after the reaction. Further, hydrazine is a toxic material having carcinogenicity and is an easily explosive compound. Therefore, it is necessary to pay close attention to the handling thereof.

Further, in the hydrazine decomposition method, there is a problem in that analysis of N-glycolylneuraminic acid cannot be performed because an N-glycolyl group is decomposed. In biopharmaceuticals and sugar chain disease markers, since the presence or absence of N-glycolylneuraminic acid which is a kind of sialic acid becomes problematic in some cases, the hydrazine decomposition method cannot be used for such purposes.

Further, liberation of O-binding sugar chains necessarily accompanies a side reaction (peeling reaction) in which sugar bound to the 3-position of N-acetylgalactosamine at a reducing end of the sugar chain is eliminated in both cases of the hydrazine decomposition method and the f-elimination method using an alkali. Even in a case where the f-elimination method using a weak base is performed in order to suppress the side reaction, there is a problem in that the peeling cannot be avoided and the liberation efficiency is significantly lowered. In addition, the reaction takes 16 hours or longer.

Further, in the method of allowing sodium borohydride to coexist in order to suppress peeling, it is not possible to perform analysis with high sensitivity using HPLC or the like because a labeling agent cannot be imparted to a reducing end.

Due to the problems described above, there has been a demand for a method for liberating N-binding sugar chains and O-binding sugar chains from proteins in a short treatment time without using a special system by employing safe and inexpensive drugs in order to analyze the sugar chains.

Solution to Problem

As the result of intensive examination conducted by the present inventors, it was found that sugar chains can be liberated from proteins using a basic catalyst in an aqueous solution in the presence of hydroxylamine, thereby completing the present invention.

In other words, the present invention includes the following aspects.

[1] A method for liberating sugar chains from a glycoprotein, including: a step of brining a reaction solution which contains hydroxylamines (a) and a basic reagent (b) into contact with the glycoprotein to obtain a mixed solution of the sugar chains liberated from the glycoprotein and the reaction solution.

[2] The method according to [1], in which the reaction solution contains 2% to 70% (w/w) of the hydroxylamines (a).

[3] The method according to [1] or [2], in which the reaction solution further contains amines (c).

[4] The method according to [3], in which the amines (c) are at least one compound selected from the group consisting of ammonia water, a methylamine aqueous solution, a dimethylamine aqueous solution, ethylamine, diethylamine, ethanolamine, ethylenediamine, butylamine, morpholine, DABCO, and anthranilic acid.

[5] The method according to any one of [1] to [4], in which the sugar chains liberated from the glycoprotein contain a sugar chain oxime.

[6] The method according to any one of [1] to [5], in which, in the step of bringing the reaction solution into contact with the glycoprotein, a pH of the reaction solution is in a range of 8 to 14.

[7] The method according to any one of [1] to [6], in which the hydroxylamines (a) are at least one compound selected from the group consisting of hydroxylamine, a salt of hydroxylamine, O-substituted hydroxylamine, and a salt of O-substituted hydroxylamine.

[8] The method according to any one of [1] to [7], in which the basic reagent (b) is at least one selected from the group consisting of a hydroxide of an alkali metal, a weak acid salt of an alkali metal, a hydroxide of an alkaline earth metal, a salt of an alkaline earth metal dissolved in an ammonia aqueous solution, and an organic base.

[9] The method according to claim 8, in which the hydroxide of an alkali metal is lithium hydroxide, sodium hydroxide, or potassium hydroxide, the weak acid salt of an alkali metal is sodium bicarbonate or sodium carbonate, the hydroxide of an alkaline earth metal is calcium hydroxide, barium hydroxide, or strontium hydroxide, the salt of an alkaline earth metal is calcium acetate, calcium chloride, barium acetate, or magnesium acetate, and the organic base is 1,8-diazabicyclo[5.4.0]undec-7-ene, 1,5,7-triazabicyclo[4.4.0]dec-5-ene, 7-methyl-1,5,7-triazabicyclo[4.4.0]dec-5-ene, 1,1,3,3-tetramethylguanidine, 2-tert-butyl-1,1,3,3-tetramethylguanidine, or cetyltrimethylammonium hydroxide.

[10] The method according to any one of [1] to [9], further including: a step of adding a ketone, an aldehyde, or an acid anhydride to the mixed solution and converting the hydroxylamines (a) remaining in the mixed solution to a ketoxime, an aldoxime, or an amide; a step of bringing the mixed solution into contact with a solid phase having an affinity for sugar chains so that the sugar chains liberated from the glycoprotein are adsorbed on the solid phase; and a step of eluting the sugar chains from the solid phase.

[11] A method for analyzing sugar chains of a glycoprotein, including: a step of liberating sugar chains from a glycoprotein using the method according to any one of claims 1 to 10; and a step of labeling the liberated sugar chains, which includes labeling of a sugar chain oxime.

[12] A kit for liberating sugar chains from a glycoprotein, including: hydroxylamines (a); and a basic reagent (b).

[13] The kit according to [12], further including: amines (c).

[14] The kit according to [12] or [13], further including: a ketone, an aldehyde, or an acid anhydride; and a solid phase having an affinity for sugar chains.

[15] The kit according to any one of [12] to [14], further including: a description for performing the method according to any one of [1] to [10].

[16] A kit for liberating sugar chains from a glycoprotein, including: a basic reagent (b) and amines (c) for being used by combining with hydroxylamines (a).

[17] The kit according to [16], further including: a ketone, an aldehyde, or an acid anhydride; and a solid phase having an affinity for sugar chains.

[18] The kit according to [16] or [17], further including: a description for performing the method according to any one of [1] to [10].

[19] A device which liberates sugar chains from a glycoprotein, including: a container holding portion which holds a container in which a sample containing a glycoprotein is accommodated; and a reagent introduction unit which introduces a reagent into the container, in which the reagent introduction unit includes a reaction solution introduction unit which introduces a reaction solution containing hydroxylamines (a) and a basic reagent (b) into the container.

[20] The device according to [19], in which the reagent introduction unit further includes a ketone introduction unit which introduces a ketone into the container, an aldehyde introduction unit which introduces an aldehyde into the container, or an acid anhydride introduction unit which introduces an acid anhydride into the container.

[21] The device according to [19] or [20], further including: a solid phase holding portion which holds a container containing a solid phase having an affinity for sugar chains.

The present invention may also include the following aspects.

[1] A method for liberating sugar chains from a glycoprotein, including: a step of brining a reaction solution which contains hydroxylamines (a) and a basic reagent (b) into contact with the glycoprotein, in which the reaction solution contains 2% to 50% (w/w) of the hydroxylamines (a).

Here, according to the embodiment of the present invention,

[2] The method for liberating sugar chains from a glycoprotein according to [1], in which the reaction solution further contains amines (c).

Further, according to the embodiment of the present invention,

[3] The method for liberating sugar chains from a glycoprotein according to [1] or [2], in which the sugar chains liberated from the glycoprotein contain a sugar chain oxime.

Further, according to the embodiment of the present invention,

[4] The method for liberating sugar chains from a glycoprotein according to any one of [1] to [3], in which, in the step of bringing the reaction solution into contact with the glycoprotein, a pH of the reaction solution is in a range of 8 to 14.

Further, according to the embodiment of the present invention,

[5] The method for liberating sugar chains from a glycoprotein according to any one of [1] to [4], in which the hydroxylamines (a) are at least one compound selected from the group consisting of hydroxylamine, salts of hydroxylamine, O-substituted hydroxylamine, and salts of O-substituted hydroxylamine.

Further, according to the embodiment of the present invention,

[6] The method for liberating sugar chains from a glycoprotein according to any one of [1] to [5], in which the basic reagent (b) is at least one selected from the group consisting of a hydroxide of an alkali metal, a weak acid salt of an alkali metal, a hydroxide of an alkaline earth, a salt of an alkaline earth dissolved in an ammonia aqueous solution, and an organic base.

Further, according to the embodiment of the present invention,

[7] The method for liberating sugar chains from a glycoprotein according to [6], in which the hydroxide of an alkali metal, the weak acid group of an alkali metal, or the hydroxide of an alkaline earth is at least one selected from the group consisting of lithium hydroxide, sodium hydroxide, potassium hydroxide, sodium bicarbonate, sodium carbonate, calcium hydroxide, barium hydroxide, and strontium hydroxide, and the salt of an alkaline earth dissolved in an ammonia aqueous solution is at least one selected from the group consisting of calcium acetate, calcium chloride, barium acetate, and magnesium acetate.

Further, according to the embodiment of the present invention,

[8] The method for liberating sugar chains from a glycoprotein according to [6], in which the organic base is at least one selected from the group consisting of 1,8-diazabicyclo[5.4.0]undec-7-ene, 1,5,7-triazabicyclo[4.4.0]dec-5-ene, 7-methyl-1,5,7-triazabicyclo[4.4.0]dec-5-ene, 1,1,3,3-tetramethylguanidine, 2-tert-butyl-1,1,3,3-tetramethylguanidine, and cetyltrimethylammonium hydroxide.

Further, according to the embodiment of the present invention,

[9] The method for liberating sugar chains from a glycoprotein according to any one of [1] to [6], in which the amines (c) are at least one compound selected from the group consisting of ammonia, methylamine, dimethylamine, ethylamine, diethylamine, ethanolamine, ethylenediamine, butylamine, morpholine, DABCO, and anthranilic acid.

Further, according to another embodiment of the present invention,

[10] A method for analyzing sugar chains of a glycoprotein, including: a step of liberating sugar chains from a glycoprotein using the method according to any one of claims 1 to 9; and a step of labeling the liberated sugar chains, which includes labeling of a sugar chain oxime.

Further, according to still another embodiment of the present invention,

[11] A kit for liberating sugar chains from a glycoprotein, including: hydroxylamines (a); and a basic reagent (b).

Further, according to the embodiment of the present invention,

[12] The kit for liberating sugar chains from a glycoprotein according to [11], further including: amines (a).

Further, according to an embodiment of the present invention,

[13] A kit for liberating sugar chains from a glycoprotein, including: a basic reagent (b) and amines (c) for being used by combining with hydroxylamines (a).

Advantageous Effects of Invention

According to the method of the present invention, it is possible to liberate sugar chains from a glycoprotein in a short treatment time while suppressing decomposition of the sugar chains by using safe and inexpensive drugs and to recover the liberated sugar chains as a mixture containing a sugar chain oxime.

Particularly, in the method for liberating N-binding sugar chains from a glycoprotein, according to the hydrazine decomposition method of the related art, it is not possible to analyze N-glycolylneuraminic acid because the N-glycolyl group is decomposed. However, according to the present method, it is possible to liberate sugar chains while suppressing decomposition of the N-glycolyl group.

DESCRIPTION OF EMBODIMENTS

Figure 1:
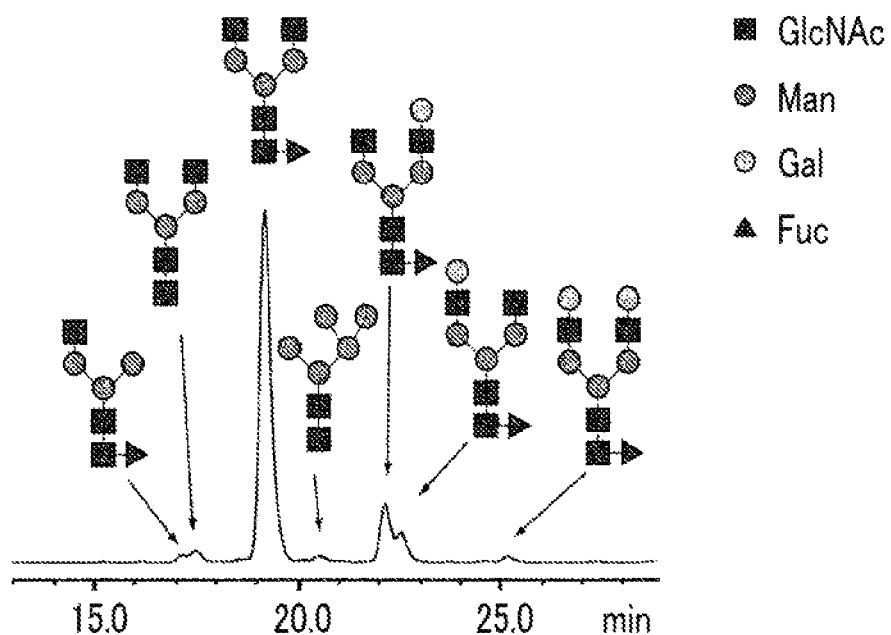
FIG. 1 shows an HPLC chromatogram of N-binding sugar chains liberated from a monoclonal antibody (IgG) in Example 1.

In the present specification, a "glycoprotein" indicates a protein in which at least one or more O-binding sugar chains or N-binding sugar chains are bound to the amino acid sequence of the protein. The glycoprotein to which the present invention can be applied is not particularly limited and may be natural or synthesized.

Further, "sugar chains" include O-binding sugar chains and N-binding sugar chains. The O-binding sugar chains each have a structure in which a sugar chain is bound through a —OH group contained in each amino acid side chain in an amino acid residue of serine (Ser) or threonine (Thr) of a protein. Further, the O-binding sugar chains are classified into 1 to 8 types depending on the structure of a core. Further, N-binding sugar chains indicate sugar chains bound to a nitrogen atom of an amide group of an asparagine residue side chain of a protein. The N-binding sugar chains include those forming branches using mannose as a base point, and examples thereof include two branched-chains, three branched-chains, and four branched-chains. Further, the N-binding sugar chains can be classified into a basic type, a high mannose type, a hybrid type, a complex type, and the like.

In the present invention, both of the O-binding sugar chains and the N-binding sugar chains can be used as a target to be liberated from a glycoprotein.

[Method for Liberating Sugar Chains from Glycoprotein]

According to an embodiment, the present invention provides a method for liberating sugar chains from a glycoprotein, including: a step of brining a reaction solution which contains hydroxylamines (a) and a basic reagent (b) into contact with the glycoprotein to obtain a mixed solution of sugar chains liberated from the glycoprotein and the reaction solution. Sugar chains can be liberated from the glycoprotein by bringing the reaction solution containing hydroxylamines (a) and a basic reagent (b) into contact with the glycoprotein.

Here, the expression "the reaction solution containing hydroxylamines (a) and a basic reagent (b) is brought into contact with a glycoprotein" is not limited as long as the glycoprotein, the hydroxylamines (a), and the basic reagent (b) finally come into contact with one another, and the mixing order does not matter. For example, the hydroxylamines are added to the glycoprotein, and then the basic reagent (b) may be added thereto. Alternatively, first, the basic reagent (b) is added to the glycoprotein, and then the hydroxylamines (a) may be added thereto. Alternatively, first, the hydroxylamines (a) and the basic reagent (b) are mixed with each other, and then the glycoprotein may be added to the mixture. Further, in a case of O-binding sugar chains, it is preferable that the hydroxylamines are added in advance in order to suppress decomposition of sugar chains.

Here, examples of the "hydroxylamines (a)" which can be used in the present embodiment include hydroxylamine, a salt of hydroxylamine, O-substituted hydroxylamine, and a salt of O-substituted hydroxylamine. Specifically, although not limited to the following, at least one compound selected from hydroxylamine hydrochloride, a hydroxylamine aqueous solution, hydroxylamine sulfate, hydroxylamine phosphate, O-methylhydroxylamine hydrochloride, O-methylhydroxylamine hydrochloride, O-ethylhydroxylamine hydrochloride, O-(tetrahydro-2H-pyran-2-yl)hydroxylamine, nitrobenzylhydroxylamine hydrochloride, O-tert-butyldimethylsilylhydroxylamine, and O-trimethylsilylhydroxylamine may be exemplified. Further, two or more of the above-described components may be used in combination. In a preferred embodiment, the "hydroxylamines (a)" indicate a hydroxylamine aqueous solution.

The final concentration of the "hydroxylamines (a)" in the reaction solution can be set to be in a range of, for example, 2% to 70% (w/w) or 2% to 50% (w/w). However, the concentration is not limited to be in the above-described range and can be appropriately adjusted depending on the type of a target glycoprotein, other components (amines, basic reagents, and other additives) in the reaction solution, and the reaction conditions (the time, the temperature, and the like) by those skilled in the art.

The present inventors clarified that the final concentration of the "hydroxylamines (a)" is preferably as high as possible, particularly in a case of liberating O-binding sugar chains. Therefore, in the case of liberating O-binding sugar chains, the final concentration of the "hydroxylamines (a)" may be in a range of, for example, 10% to 70% (w/w) or 30% to 60% (w/w), and particularly suitably 50% (w/w).

Further, in a case of liberating N-binding sugar chains, the final concentration of the "hydroxylamines (a)" may be set to be in a range of 2% to 50% (w/w) and preferably in a range of 10% to 20% (w/w). In a more preferred embodiment, the final concentration is 10% (w/w).

In a case where hydroxylamine is used as the "hydroxylamines (a)", by setting the concentration of the hydroxylamine to be greater than 2% (w/w) and 50% (w/w) or less, a sufficiently high recovery amount of sugar chains is obtained and the hydroxylamine tends to be stable.

Further, as the "basic reagent (b)" which can be used in the present embodiment, at least one compound selected from the group consisting of a hydroxide of an alkali metal, a weak acid salt of an alkali metal, a hydroxide of an alkaline earth metal, a salt of an alkaline earth metal dissolved in an ammonia aqueous solution, and an organic base may be exemplified.

Although not limited to the following, examples of the hydroxide of an alkali metal include lithium hydroxide, sodium hydroxide, and potassium hydroxide.

Although not limited to the following, examples of the weak acid salt of an alkali metal include sodium bicarbonate and sodium carbonate.

Although not limited to the following, examples of the hydroxide of an alkaline earth metal include calcium hydroxide, barium hydroxide, and strontium hydroxide, Although not limited to the following, examples of the salt of an alkaline earth metal dissolved in ammonia water include calcium acetate, calcium chloride, barium acetate, and magnesium acetate.

Among these, lithium hydroxide is particularly preferable.

Although not limited to the following, examples of the organic base include DBU: 1,8-diazabicyclo[5.4.0]undec-7-ene, TBD: 1,5,7-triazabicyclo[4.4.0]dec-5-ene, MTBD: 7-methyl-1,5,7-triazabicyclo[4.4.0]dec-5-ene, TMG: 1,1,3,3-tetramethylguanidine, t-BuTMG: 2-tert-butyl-1,1,3,3-tetramethylguanidine, DBN: 1,5-diazabicyclo[4.3.0]non-5-ene, and CTAH: cetyltrimethylammonium hydroxide. Further, two or more of the above-described compounds may be used in combination. In a preferred embodiment, the "organic base" indicates an organic strong base (pKa of 12 or greater), and specific examples thereof include DBU, TMG, TBD, MTBD, and CTAH. From the viewpoint that the base after the reaction can be removed by being washed with an organic solvent, it is preferable to use DBU, TMG, TBD, MTBD, or CTAH as the "organic base".

The final concentration of the "basic reagent (b)" in the reaction solution can be set to be in a range of, for example, 2 mM to 2 M. However, the concentration is not limited to be in the above-described range and can be appropriately adjusted depending on the type of a target glycoprotein, other components (hydroxylamines and other additives) in the reaction solution, and the reaction conditions (the time, the temperature, and the like) by those skilled in the art. Further, for example, in a case where lithium hydroxide is used as the "basic reagent (b)", the final concentration thereof can be set to be in a range of 6 mM to 1 M and preferably in a range of 100 mM to 500 mM. In a more preferred embodiment, the final concentration thereof is in a range of 100 mM to 200 mM. In a case where the concentration of the basic reagent is less than 2 mM, the reaction time becomes longer, which is not preferable. Further, in a case where the concentration thereof is greater than 2 M, the recovery rate of sugar chains is decreased, which is not preferable.

According to the method for liberating sugar chains from a glycoprotein of the present embodiment, the sugar chains are liberated from the glycoprotein by bringing the reaction solution containing the hydroxylamines (a) and the basic reagent (b) into contact with the glycoprotein. At this time, the content of the hydroxylamines (a) is in a range of 2% to 70% (w/w) with respect to the content of the reaction solution.

At this time, the molar ratio between the hydroxylamines (a) and the basic reagent (b) in the reaction solution is set to be preferably in a range of 1:1 to 300:1 and more preferably in a range of 3:1 to 200:1. In a case where the molar ratio between the hydroxylamines (a) and the basic reagent (b) is set to be in the above-described range, the decomposition reaction of the liberated sugar chains can be suppressed.

Further, the pH of the reaction solution can be set to be in a range of 8 to 14 and more preferably in a range of 10 to 13.

In the step of bringing the reaction solution into contact with the target glycoprotein, the conditions of the temperature and the reaction time are not particularly limited as long as sugar chains can be liberated from the target glycoprotein and can be appropriately set depending on the conditions of the type, the concentration, and the like of the target glycoprotein, the hydroxylamines, and the basic reagent by those skilled in the art. Further, the temperature can be set to be in a range of, for example, room temperature to 80° C. In addition, since an N-glycolyl group or the like tends to be decomposed at the time of causing a reaction at a high temperature, it is preferable that the temperature is set to 50° C. or lower in a case where a glycoprotein having unknown sugar chains is used as a target. Further, the reaction time can be set to be in a range of 5 minutes to 16 hours depending on the conditions.

Further, according to the method for liberating sugar chains from a glycoprotein of the present embodiment, in an embodiment, "amines (c)" can be further added to the reaction solution. Although not limited to the following, as the "amines (c)" which can be used in the present embodiment, at least one compound selected from the group consisting of ammonia water, a methylamine aqueous solution, a dimethylamine aqueous solution, ethylamine, diethylamine, ethanolamine, ethylenediamine, butylamine, morpholine, DABCO, and anthranilic acid may be exemplified.

Further, two or more of the above-described compounds may be used in combination. In a preferred embodiment, the "amines (c)" are ammonia water, morpholine, DABCO, and anthranilic acid. From the viewpoints of suppressing peeling, isomerization, and decomposition of an amide, it is preferable that ammonia water, morpholine, DABCO, anthranilic acid, and the like are used as the "amines (c)". From the viewpoint of suppressing isomerization which is a side reaction at the time of liberating N-binding sugar chains, it is particularly preferable that morpholine, DABCO, anthranilic acid, and the like which have a lower pKa than that of ammonia are used.

The final concentration of the "amines (c)" in the reaction solution can be set to be in a range of, for example, 40 mM to 15 M. However, the concentration is not limited to be in the above-described range and can be appropriately adjusted depending on the type of a target glycoprotein, other components (hydroxylamines, basic reagents, and other additives) in the reaction solution, and the reaction conditions (the time, the temperature, and the like) by those skilled in the art. Further, for example, in a case where ammonia water is used as the "amines (c), the final concentration of ammonia in the reaction solution can be set to be in a range of 2% to 25% (w/w) and preferably in a range of 10% to 20% (w/w). In a more preferred embodiment, the final concentration thereof is 20% (w/w).

[Method for Analyzing Sugar Chains]

According to an embodiment, the present invention provides a method for analyzing sugar chains of a glycoprotein, including: a step of liberating sugar chains from a glycoprotein using the above-described method; and a step of labeling the liberated sugar chains.

According to the analysis method of the present embodiment, a sugar chain oxime is also labeled in the step of labeling the liberated sugar chains.

The reaction solution after sugar chains are liberated from the glycoprotein can be used for analyzing the sugar chains contained in the reaction solution by performing a desalting treatment according to a known method (for example, a solid phase extraction cartridge filled with graphite carbon).

As a method for analyzing liberated sugar chains in the solution, a known method can be appropriately used. For example, a fluorescent labeling method of using picoline borane and 2-aminobenzamide can be used, as employed in the examples below.

Further, the sugar chains liberated according to the above-described method, some of the aldehyde type sugar chains form a sugar chain oxime. In other words, in the methods of the related art, in a case where an aldehyde group serving as a functional group of liberated sugar chains is reduced and converted to alditol, direct fluorescent labeling cannot be made. Further, in the methods of the related art, in a case where an aldehyde group serving as a functional group of sugar chains is converted to a hydrazone by hydrazine, it is necessary to return the original liberated sugar chains by carrying out a re-acetylation operation in order to impart fluorescent labeling.

On the contrary, according to the above-described method, liberated sugar chains can be obtained as a sugar chain oxime which can be directly labeled. In other words, the sugar chains liberated from the glycoprotein according to the method of the present embodiment contains a sugar chain oxime. The sugar chain oxime can be directly labeled.

Therefore, liberated sugar chains obtained according to the above-described method can be obtained in the solution as a mixture of a glycosylamine, a sugar chain oxime, and a typical sugar chain containing a hemiacetal hydroxyl group in a reducing end, and these can be collectively labeled.

Meanwhile, as described above, the present inventors clarified that the final concentration of the "hydroxylamines (a)" is preferably as high as possible, particularly in a case of liberating O-binding sugar chains.

However, in a case where the mixed solution of the glycoprotein and the reaction solution contains hydroxylamines (a) with a high concentration, unreacted hydroxylamines (a) may remain in the mixed solution after liberation of sugar chains. Since the unreacted hydroxylamines (a) inhibit the fluorescent labeling reaction of sugar chains, it is preferable that the unreacted hydroxylamines (a) are removed.

Here, the above-described method may further include additional steps of removing the unreacted hydroxylamines (a). In other words, the above-described method may further include a step of adding a ketone, an aldehyde, or an acid anhydride to the mixed solution of the glycoprotein and the reaction solution and converting the hydroxylamines (a) remaining in the mixed solution into a ketoxime, an aldoxime, or an amide; a step of bringing the mixed solution into contact with a solid phase having an affinity for sugar chains so that the sugar chains liberated from the glycoprotein are adsorbed on the solid phase; and a step of eluting the sugar chains from the solid phase.

The hydroxylamines (a) can be converted to a ketoxime by reacting with a ketone. Further, the hydroxylamines (a) can be converted to an aldoxime by reacting with an aldehyde. Further, the hydroxylamines (a) can be converted to an amide by reacting with an acid anhydride.

As the ketone, acetone, methyl ethyl ketone, methyl isobutyl ketone, 4-hydroxybutanone, or the like can be used. Further, as the aldehyde, salicylaldehyde, benzaldehyde, 4-hydroxybenzaldehyde, or the like can be used. Further, as the acid anhydride, acetic anhydride, succinic anhydride, or the like can be used.

Next, sugar chains are recovered from the above-described mixed solution. Specifically, the sugar chains can be recovered from the above-described mixed solution by bringing the mixed solution into contact with a solid phase having an affinity for sugar chains, adsorbing the sugar chains liberated from the glycoprotein on the solid phase, and eluting the sugar chains from the solid phase.

By performing the above-described operation, the unreacted hydroxylamines (a) can be removed from the sugar chains liberated from the glycoprotein.

The solid phase having an affinity for sugar chains is not particularly limited, and examples thereof include hydrophilic carriers such as graphite carbon, crystalline cellulose, silica, and monolith silica. Among these, monolith silica is particularly suitable. The monolith silica indicates filter-like porous continuous silica having a three-dimensional network structure and has advantages that the liquid permeability is excellent compared to particulate silica of the related art and the dead volume is small. The monolith silica may be fixed to a column-like container such as a multi-well plate.

In the pores size of monolith silica, the diameter of continuous pores (through pores) is preferably in a range of 1 to 100 m, more preferably in a range of 1 to 50 m, still more preferably in a range of 1 to 30 µm, and particularly preferably in a range of 1 to 20 µm.

After the mixed solution to which a ketone, an aldehyde, or an acid anhydride has been added is poured into a column or multi-well plate to which the hydrophilic carrier has been fixed, allowed to pass therethrough using a method of natural fall, suction, pressurization, centrifugation, or the like, and washed with a washing solution, an eluate may be added thereto to elute sugar chains.

The mixed solution, to which a ketone, an aldehyde, or an acid anhydride has been added, which is to be applied to the hydrophilic carrier contains preferably 90% by volume or greater of an organic solvent and more preferably 95% by volume or greater of an organic solvent. Examples of the organic solvent include acetonitrile, methanol, ethanol, 2-propanol, hexane, ethyl acetate, methylene chloride, and tetrahydrofuran. Among these, acetonitrile is particularly preferable.

It is preferable that the hydrophilic carrier is washed with a washing solution after the mixed solution to which a ketone, an aldehyde, or an acid anhydride has been added is applied to the hydrophilic carrier. It is preferable that the washing solution contains 90% by volume or greater of an organic solvent and 10% by volume or less of water and more preferable that the washing solution contains 95% by volume or greater of an organic solvent and 5% by volume or less of water. Examples of the organic solvent contained in the washing solution include acetonitrile, methanol, ethanol, 2-propanol, hexane, ethyl acetate, methylene chloride, and tetrahydrofuran. Among these, acetonitrile is particularly preferable. In addition, washing solutions having different compositions may be used. For example, the hydrophilic carrier is washed with 100% acetonitrile and then washed with a mixed solution containing acetonitrile and water at a mixing ratio of 95:5 (v/v).

After the washing operation, the eluate is added to the hydrophilic carrier so that sugar chains are eluted. It is preferable that the eluate contains 10% by volume or greater of water and more preferable that the eluate contains 50% by volume or greater of water. In addition, water is particularly preferable. As a component other than water to be contained in the eluate, an organic solvent selected from acetonitrile and alcohols represented by methanol, ethanol, propanol, and butanol is preferable. The eluted sugar chains can be provided for the fluorescent labeling reaction.

According to an embodiment, the present invention provides a kit for liberating sugar chains from a glycoprotein, including: hydroxylamines (a) and a basic reagent (b). Further, the kit of the present embodiment is a kit which further includes amines (c) in addition to the hydroxylamines (a) and the basic reagent (b) in an embodiment. Further, the kit for liberating sugar chains from the glycoprotein according to the present embodiment is a kit which contains a basic reagent (b) and amines (c) for being used by combining with hydroxylamines (a) in another embodiment.

The kit according to the present embodiment may further include a reagent (the hydroxylamines (a), the amines (c), other additives, or the like) used for the step of liberating sugar chains from the glycoprotein, a ketone, an aldehyde, or an acid anhydride, a carrier (a solid phase having an affinity for sugar chains) used for purifying sugar chains, a reagent (a fluorescent reagent or the like) used for analyzing sugar chains, a detection device, a description describing specific procedures of the method for liberating sugar chains from the glycoprotein, and the like.

[Device]

According to an embodiment, the present invention provides a device for liberating sugar chains from a glycoprotein, including: a container holding portion which holds a container in which a sample containing a glycoprotein is accommodated; and a reagent introduction unit which introduces a reagent into the container, in which the reagent introduction unit includes a reaction solution introduction unit which introduces a reaction solution containing hydroxylamines (a) and a basic reagent (b) into the container. Further, the configuration of the device described below is a merely an example, and the device of the present embodiment is not limited to this configuration.

Figure 10:
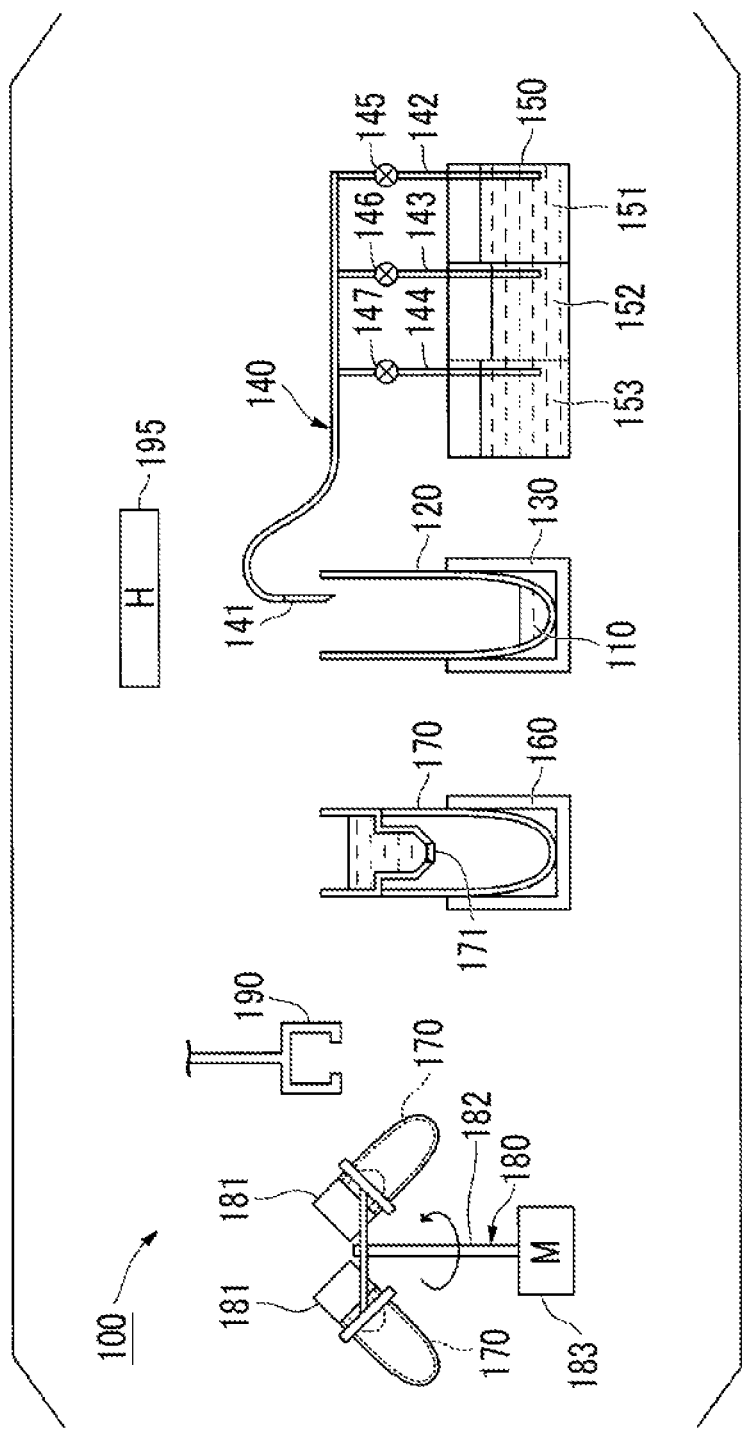
FIG. 10 is a schematic view for explaining an embodiment of a device that liberates sugar chains from a glycoprotein.

FIG. 10 is a schematic view for explaining the device according to the present embodiment. A device 100 includes a container holding portion 130 which holds a container 120 in which a sample 110 containing a glycoprotein is accommodated; and a reagent introduction unit 140 which introduces a reagent into the container 120, and the reagent introduction unit 140 includes a reaction solution introduction unit 141 which introduces a reaction solution 151 containing hydroxylamines (a) and a basic reagent (b) into the container 120.

The container holding portion 130 is used for holding the container 120 in which the sample 110 that contains the glycoprotein is accommodated. The mode in which the container holding portion 130 holds the container 120 is not particularly limited, and a mode in which most of the container is fitted to and held by a holding hole or a holding pore of the container holding portion 130 may be exemplified. In addition, a mode in which an engagement recess (engagement projection) of the container is engaged with and held by an engagement projection (engagement recess) of the container holding portion or a mode in which the container is clipped and held by a clipping portion of the container holding portion may be exemplified.

The reagent introduction unit 140 is used for introducing a reagent into the container 120 held by the container holding portion 130 or into a container 170 held by a solid phase holding portion 160 described below. The reagent introduction unit 140 includes at least the reaction solution introduction unit 141 that introduces the reaction solution 151 containing the hydroxylamines (a) and the basic reagent (b) into the container 120.

The reagent introduction unit 140 may further include a ketone introduction unit that introduces a ketone into the container 120, an aldehyde introduction unit that introduces an aldehyde into the container, or an acid anhydride introduction unit that introduces an acid anhydride.

In the example of FIG. 10, the reagent introduction unit 140 includes a tank 150 which accommodates the reaction solution 151, a ketone, aldehyde, or acid anhydride 152, and a labeling reagent 153; liquid supply tubes (142, 143, and 144) which supply each reagent accommodated in the tank 150; valves (145, 146, and 147) which control liquid supply of each reagent; and the introduction unit 141 which introduces each reagent into the container 120 or the container 170. In the example of FIG. 10, the introduction unit 141 also serves as the reaction solution introduction unit; the ketone introduction unit, the aldehyde introduction unit, or the acid anhydride introduction unit, and the labeling reagent introduction unit. The reaction solution 151 contains the hydroxylamines (a) and the basic reagent (b).

The mode in which the reagent introduction unit 140 introduces a reagent into the container 120 or the container 170 is not particularly limited, and a mode in which each liquid is supplied to the inside of the container 120 or the container 170 through a tubular member from liquid supply sources (151, 152, and 153) where each liquid to be supplied is stored is exemplified. In addition, a mode in which the liquid collected in the tubular member is poured into the reaction container may be exemplified.

The reaction solution introduction unit, the ketone introduction unit, or the aldehyde introduction unit, and the labeling reagent introduction unit may be formed as separate independent constituent members or formed as the same constituent members.

The device 100 may further include a solid phase holding portion 160 which holds the container 170 containing a solid phase 171 with an affinity for sugar chains. The structure of the solid phase holding portion 160 may be the same as the structure of the container holding portion 130. Further, the device 100 may further include a solid-liquid separation unit 180 which performs solid-liquid separation on the contents of the container 170. In a case where the device 100 includes the solid-liquid separation unit 180, the solid-liquid separation unit 180 separates a solid and a liquid from the contents contained in the container 170. Here, a solid substantially indicates the solid phase 10 and sugar chains adsorbed thereon.

The specific separation form of the solid-liquid separation unit 180 is not particularly limited and may be any of centrifugation, pressure reduction, and pressurization. In the example of FIG. 10, the separation form of the solid-liquid separation unit 180 is centrifugation. The solid-liquid separation unit 180 includes a rack 181 which holds the container 170; a drive shaft 182; and a motor 183.

As in the example of FIG. 10, the solid-liquid separation unit 180 may be formed as a constituent member independent from the solid phase holding portion 160. In this case, the device 100 may include a container transfer unit 190 which automatically transfers the container 170 to the solid-liquid separation unit 180 from the solid phase holding portion 160. The container transfer unit 190 may include an arm which performs an operation of gripping, opening, and moving the container 170; and an arm control unit which controls the operation of the arm.

The liquid is recovered in the lower portion of the container 170 by operating the solid-liquid separation unit 180. Therefore, for example, the sugar chains adsorbed on the solid phase 171 can be eluted so as to be recovered in the lower portion of the container 170.

The device 100 may further include a temperature adjusting unit 195 which adjusts the temperature of the contents in the container 120 or the container 170. In a case where the device 100 includes the temperature adjusting unit 195, the temperature adjusting unit 195 may have at least a heater function. The temperature adjusting unit 195 can heat the container 120 or the container 170 to a required temperature.

In the device 100, at least any of the constituent portions (for example, the introduction unit 141, the arm 190, the solid-liquid separation unit 180, and the temperature adjusting unit 195) which can be operated and preferably all of these may be automatically controlled. In this manner, preparation of sugar chains from the glycoprotein can be rapidly carried out.

EXAMPLES

The following examples are intended to be only used for exemplification and do not limit the technical scope of the present invention.

The materials or reagents are commercially available or can be obtained or prepared according to conventional methods in the technical field or according to the procedures of known literatures, unless otherwise specified.

Example 1

<Analysis of Sugar Chains of Monoclonal Antibody (IgG1)>

A monoclonal antibody (IgG1, 40 µg) was dissolved in 30 µL of a 25% ammonia aqueous solution which had been saturated with calcium acetate, 20 µL of a 50% hydroxylamine aqueous solution was added thereto, and the solution was mixed and heated at 80° C. for 1 hour using a heat block during draft. Thereafter, the reaction solution was immediately cooled in an ice bath and then neutralized with 1 N hydrochloric acid.

(Analysis of Liberated Sugar Chains)

The neutralized reaction solution was desalted using a solid phase extraction cartridge (HyperSep Hypercarb, 25 mg, manufactured by Thermo Fisher Scientific, Inc.) filled with graphite carbon, and sugar chains were subjected to fluorescent labeling using picoline borane and 2-aminobenzamide. The fluorescent-labeled sugar chains were purified by Sephadex G-15 (manufactured by GE Healthcare) and analyzed according to HPLC. The chromatogram thereof is shown in FIG. 1. In FIG. 1, the horizontal axis shows the elution time and the vertical axis shows the fluorescence intensity (relative value).

Comparative Example 1

Figure 2:
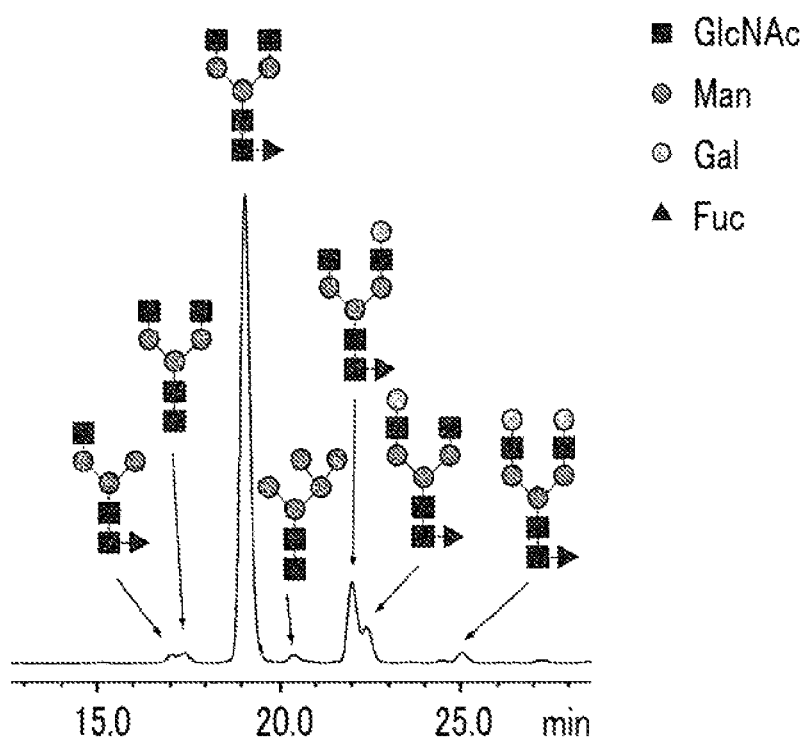
FIG. 2 shows an HPLC chromatogram of N-binding sugar chains liberated from a monoclonal antibody (IgG) according to a method of using an enzyme (PNGaseF) that liberates N-binding sugar chains in Example 1.

The reaction for separating sugar chains was performed using an enzyme (PNGaseF) in order to compare with the methods of the related art. A monoclonal antibody (IgG1, 40 µg) was dissolved in a 500 mM tris-hydrochloric acid buffer solution (pH of 8.6) containing 100 mM dithiothreitol and 0.5% SDS, and the solution was heated at 80° C. for 10 minutes. Thereafter, the solution was cooled to room temperature, 5% Nonidet P-40 (40 µL) and 15 µL of distilled water were added to the solution, 5 µL of PNGaseF (16 mU, Takara bio Inc.) was further added thereto, and the resulting solution was incubated at 37° C. for 16 hours. Thereafter, the reaction solution was immediately cooled in an ice bath and neutralized with 1 N hydrochloric acid. Next, the reaction solution was provided for a solid phase extraction cartridge SepPak C18 (50 mg, Waters Corp.) and then washed with distilled water. The filtrate and the washing solution were combined with each other, subjected to a desalting treatment using a solid phase extraction cartridge (HyperSep Hypercarb, 25 mg) according to the method described in Example 1, subjected to fluorescent labeling using 2-aminobenzamide, purified by Sephadex G-15 (manufactured by GE Healthcare), and then analyzed according to HPLC. The chromatogram thereof is shown in FIG. 2. In FIG. 2, the horizontal axis shows the elution time and the vertical axis shows the fluorescence intensity (relative value). As illustrated in FIGS. 1 and 2, it was clarified that the same chromatogram was obtained using the method of the present example as those obtained using the methods of the related art.

Example 2

<Analysis of Sugar Chains from Human Serum-Derived IgG>

(Reaction for Liberating N-Binding Sugar Chains)

20 µL of an aqueous solution containing human serum derive IgG (200 µg) was poured into a sample tube, 10 µL of a 50% hydroxylamine aqueous solution was added to the tube, 25 µL of a 25% ammonia aqueous solution and 5 µL of 1.2 M lithium hydroxide were added thereto, and the solution was mixed and heated at 50° C. for 1 hour using a heat block during draft. Thereafter, the reaction solution was immediately cooled in an ice bath and then neutralized with 1 N hydrochloric acid.

(Analysis of Liberated Sugar Chains)

Figure 3:
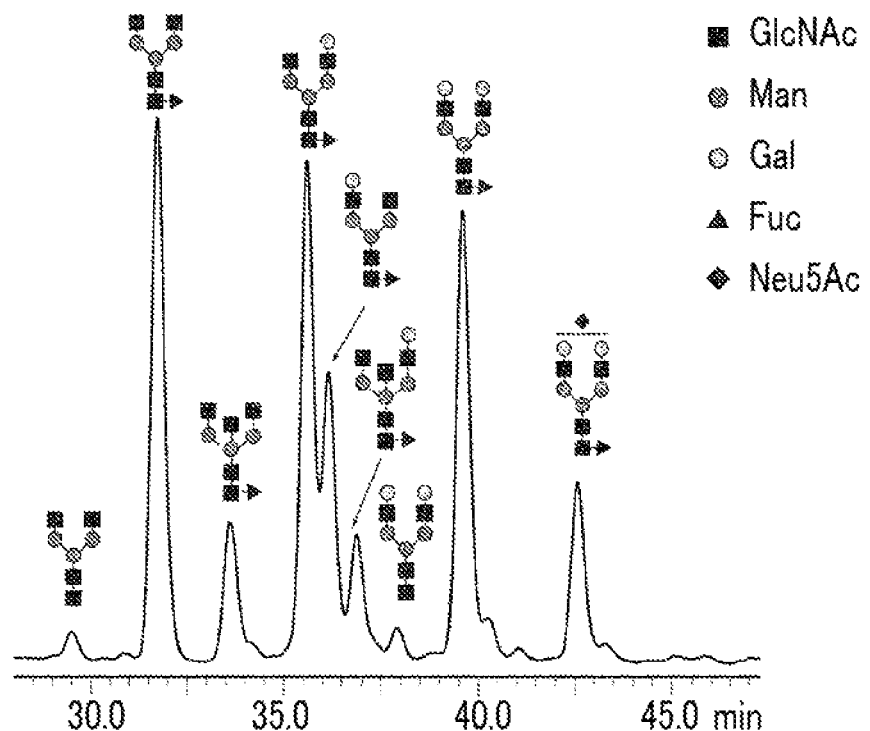
FIG. 3 shows an HPLC chromatogram of N-binding sugar chains liberated from human serum-derived IgG in Example 2.

According to the same method as in Example 1, the reaction solution was desalted, and the sugar chains were subjected to fluorescent labeling and analyzed using HPLC. The chromatogram thereof is shown in FIG. 3. In FIG. 3, the horizontal axis shows the elution time and the vertical axis shows the fluorescence intensity (relative value). As the result, the same results as the results obtained by analyzing the sugar chains liberated from human serum-derived IgG were obtained.

Example 3

<Analysis of Sugar Chains from Bovine Fetuin>
(Reaction for Liberating O-Binding Sugar Chains)

Bovine fetuin (20 µg) was dissolved in 38.5 µL of distilled water, 10 µL of 50% hydroxylamine and 1.5 µL of diazabicycloundecene were added thereto, and the solution was mixed and heated at 60° C. for 5 minutes using a heat block during draft. Thereafter, the reaction solution was immediately cooled in an ice bath and then neutralized with 1 N hydrochloric acid.

(Analysis of Liberated Sugar Chains)

Figure 4:
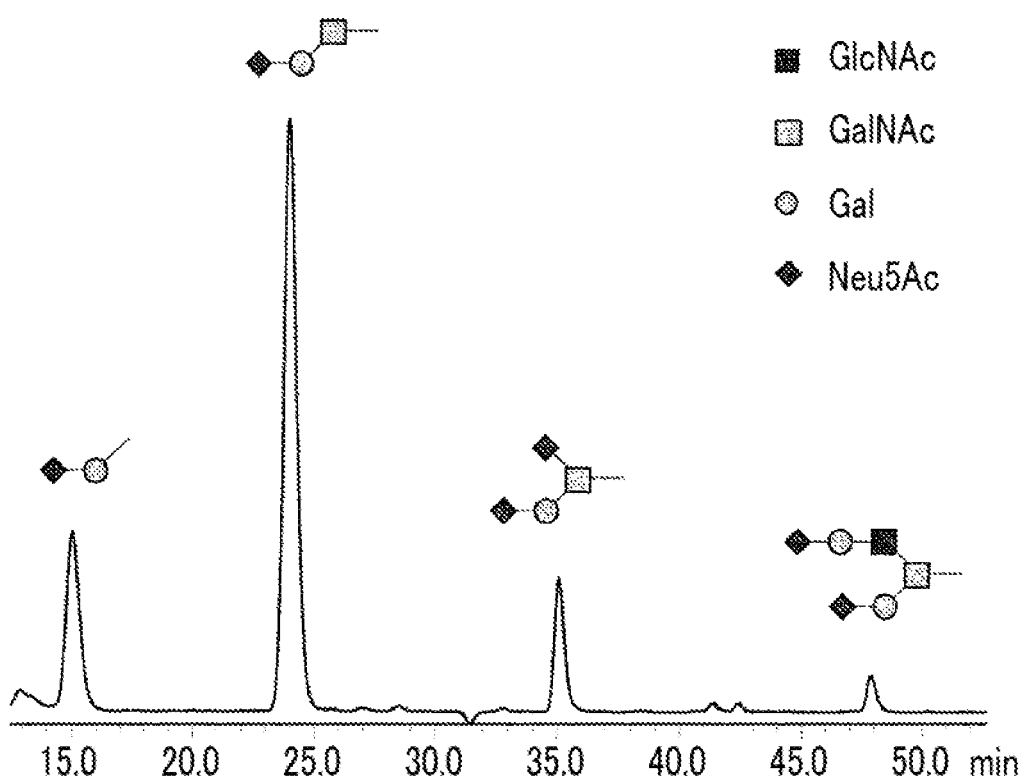
FIG. 4 shows an HPLC chromatogram of O-binding sugar chains liberated from bovine fetuin in Example 3.

According to the same method as in Example 1, the reaction solution was desalted, and the sugar chains were subjected to fluorescent labeling and analyzed using HPLC. The chromatogram thereof is shown in FIG. 4. In FIG. 4, the horizontal axis shows the elution time and the vertical axis shows the fluorescence intensity (relative value). As the result, the same results as the results obtained by analyzing the sugar chains liberated from bovine fetuin were obtained.

Example 4

<Analysis of Sugar Chains from Bovine Apo-Transferrin>
(Reaction for Liberating N-Binding Sugar Chains)

20 µL of an aqueous solution containing bovine apo-trasferrin (200 µg) was poured into a sample tube, 20 µL of a 50% hydroxylamine aqueous solution was added to the tube, 10 µL of 1.0 M lithium hydroxide was added thereto, and the solution was mixed and heated at 50° C. for 1 hour using a heat block during draft. Thereafter, the reaction solution was immediately cooled in an ice bath and then neutralized with 1 N hydrochloric acid.

(Analysis of Liberated Sugar Chains)

Figure 5:
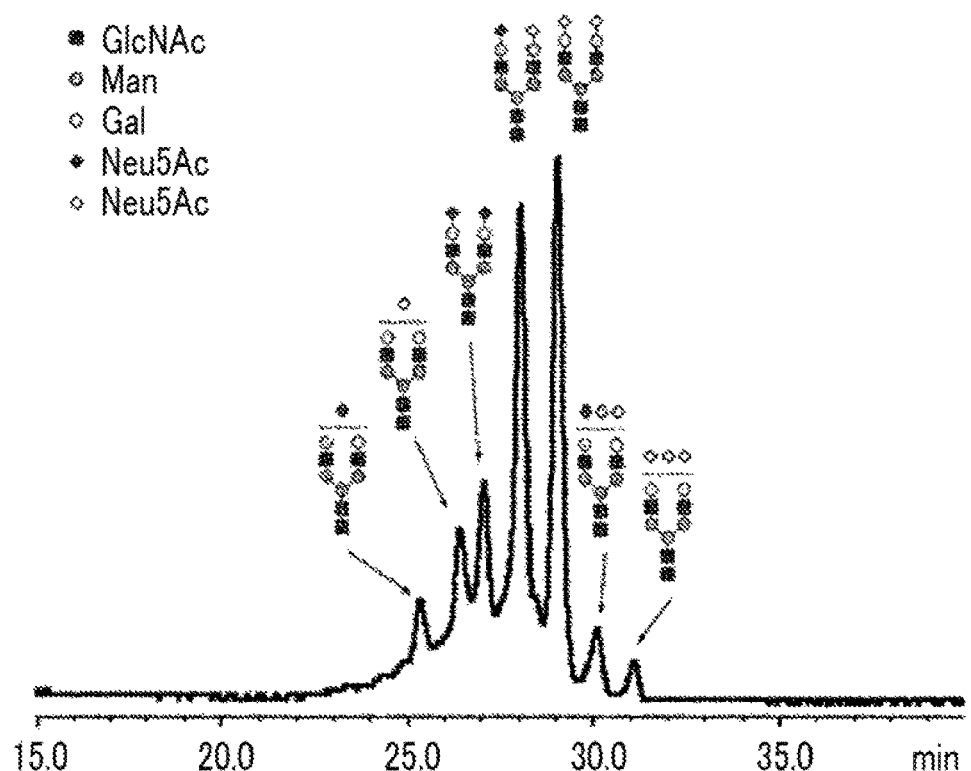
FIG. 5 shows an HPLC chromatogram of N-binding sugar chains liberated from bovine apo-trasferrin in Example 4.

According to the same method as in Example 1, the reaction solution was desalted, and the sugar chains were subjected to fluorescent labeling and analyzed using HPLC. The chromatogram thereof is shown in FIG. 5. In FIG. 5, the horizontal axis shows the elution time and the vertical axis shows the fluorescence intensity (relative value). As the result, it was clarified that sugar chains containing N-glycolylneuraminic acid can also be analyzed.

Example 5

<Analysis of Sugar Chains from Horse Radish Peroxidase>
(Reaction for Liberating N-Binding Sugar Chains)

20 µL of an aqueous solution containing horse radish peroxidase (200 µg) was poured into a sample tube, 20 µL of a 50% hydroxylamine aqueous solution was added to the tube, 10 µL of 1.0 M lithium hydroxide was added thereto, and the solution was mixed and heated at 50° C. for 1 hour using a heat block during draft. Thereafter, the reaction solution was immediately cooled in an ice bath and then neutralized with 1 N hydrochloric acid.

(Analysis of Liberated Sugar Chains)

Figure 6:
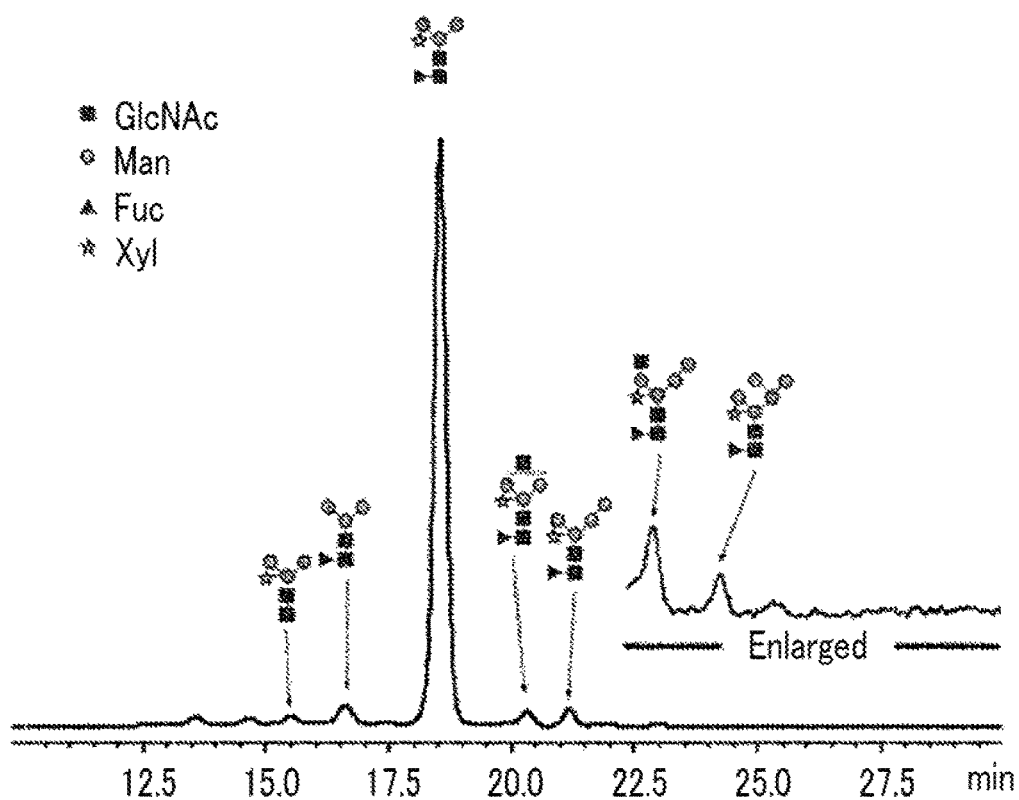
FIG. 6 shows an HPLC chromatogram of N-binding sugar chains liberated from horse radish peroxidase in Example 5.

According to the same method as in Example 1, the reaction solution was desalted, and the sugar chains were subjected to fluorescent labeling and analyzed using HPLC. The chromatogram thereof is shown in FIG. 6. In FIG. 6, the horizontal axis shows the elution time and the vertical axis shows the fluorescence intensity (relative value). As the result, it was clarified that N-binding sugar chains having fucose at the 3-position of N-acetylglucosamine at the reducing end can be analyzed.

Example 6

<Analysis of Sugar Chains from Bovine Submaxillary Gland Mucin>
(Reaction for Liberating O-Binding Sugar Chains)

20 µL of an aqueous solution containing bovine submaxillary gland mucin (50 g), 20 µL of 50% hydroxylamine, and 10 µL of diazabicycloundecene were mixed and heated at 60° C. for 5 minutes using a heat block during draft. Thereafter, the reaction solution was immediately cooled in an ice bath and then neutralized with 1 N hydrochloric acid.

(Analysis of Liberated Sugar Chains)

Figure 7:
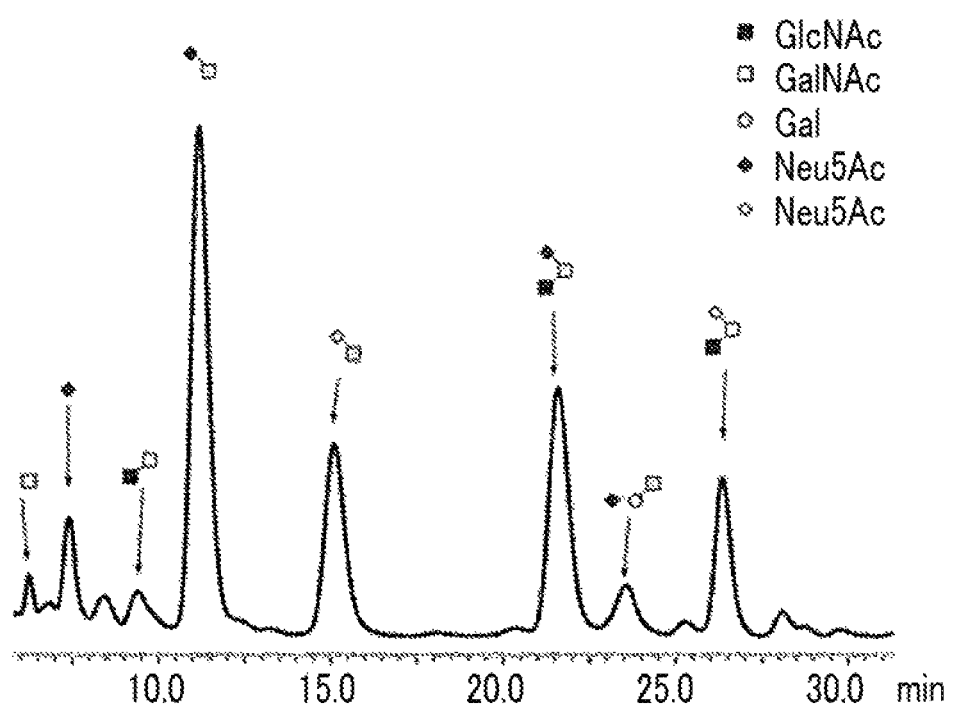
FIG. 7 shows an HPLC chromatograph of O-binding sugar chains liberated from bovine submaxillary gland mucin in Example 6.

According to the same method as in Example 1, the reaction solution was desalted, and the sugar chains were subjected to fluorescent labeling and analyzed using HPLC. The chromatogram thereof is shown in FIG. 7. In FIG. 7, the horizontal axis shows the elution time and the vertical axis shows the fluorescence intensity (relative value). As the result, the same results as those reported so far were obtained.

Example 7

<Reaction for Liberating N-Binding Sugar Chains Under Various Conditions>

In the reaction solution containing the hydroxylamines (a), the basic reagent (b), and/or the amines (c), various tests were performed by changing various conditions such as the type and the concentration of the reagent, the temperature, the reaction time, and the reaction time. The conditions and the yields in each test example are listed in Tables 1A and 1B. Further, 200 µg of human serum IgG was used as the glycoprotein in Test Examples 1 to 6, and 40 µg of a monoclonal antibody M-L001 was used as the glycoprotein in Test Examples 7 to 80. Further, the concentration of each reagent indicates the final concentration, and the yield indicates the total area value of all sugar chain peaks in HPLC. In addition, the result "A" indicates that almost the same results as the results obtained according to the methods of the related art using PNGaseF were obtained, the result "B" indicates that the yield was less than half the yield obtained according to the methods of the related art using PNGaseF, the result "C" indicates that peaks of decomposed sugar chains were detected in addition to the original sugar chains, and the result "D" indicates that the sugar chains were hardly analyzed.

TABLE 1A

| Test Example | Basic reagent | Amines | Hydroxylamines | Temperature (° C.) | Time (min) | Yield | Results |
|---|---|---|---|---|---|---|---|
| 1 | LiOH 100 mM | NH$_3$ 10% | 8.3% hydroxylamine | 50 | 60 | 4924 | A |
| 2 | LiOH 100 mM | — | 8.3% hydroxylamine | 50 | 60 | 2221 | B |
| 3 | LiOH 120 mM | NH$_3$ 12.5% | 10% hydroxylamine | 80 | 60 | 2458 | A |
| 4 | sat. Ca(OH)$_2$ | NH$_3$ 15% | 10% hydroxylamine | 80 | 60 | 2495 | A |
| 5 | sat. Ca(Cl)$_2$ | NH$_3$ 15% | 10% hydroxylamine | 80 | 60 | 1879 | B |
| 6 | sat. Ca(Oac)$_2$ | NH$_3$ 15% | 10% hydroxylamine | 80 | 60 | 1455 | B |
| 7 | sat. Ca(Oac) | NH$_3$ 25% | — | 80 | 60 | 301 | C |
| 8 | 98% sat. Ca(Oac) | NH$_3$ 24.5% | 0.5% hydroxylamine | 80 | 60 | 182 | C |
| 9 | 96% sat. Ca(Oac) | NH$_3$ 24% | 2% hydroxylamine | 80 | 60 | 2281 | A |
| 10 | 90% sat. Ca(Oac) | NH$_3$ 22.5% | 5% hydroxylamine | 80 | 60 | 2429 | A |
| 11 | 80% sat. Ca(Oac) | NH$_3$ 20% | 10% hydroxylamine | 80 | 60 | 2911 | A |
| 12 | 60% sat. Ca(Oac) | NH$_3$ 15% | 20% hydroxylamine | 80 | 60 | 2798 | A |
| 13 | 20% sat. Ca(Oac) | NH$_3$ 5% | 40% hydroxylamine | 80 | 60 | 1212 | B |
| 14 | — | — | 50% hydroxylamine | 80 | 60 | 653 | C |
| 15 | 80% sat. Ca(Oac) | NH$_3$ 20% | 10% hydroxylamine | 80 | 10 | 539 | C |
| 16 | 80% sat. Ca(Oac) | NH$_3$ 20% | 10% hydroxylamine | 80 | 30 | 1167 | B |
| 17 | 80% sat. Ca(Oac) | NH$_3$ 20% | 10% hydroxylamine | 80 | 60 | 1135 | B |
| 18 | 80% sat. Ca(Oac) | NH$_3$ 20% | 10% hydroxylamine | 80 | 120 | 1796 | B |
| 19 | 80% sat. Ca(Oac) | NH$_3$ 20% | 10% hydroxylamine | 80 | 240 | 1069 | C |
| 20 | 80% sat. Ca(Oac) | NH$_3$ 20% | 10% hydroxylamine | 80 | 360 | 895 | C |
| 21 | 100 mM NaHCO$_3$ | NH$_3$ 20% | 10% hydroxylamine | 80 | 60 | 2421 | A |
| 22 | 100 mM Na$_2$CO$_3$ | NH$_3$ 20% | 10% hydroxylamine | 80 | 60 | 2515 | A |
| 23 | 100 mM NaOH | NH$_3$ 20% | 10% hydroxylamine | 80 | 60 | 2340 | A |
| 24 | 100 mM KOH | NH$_3$ 20% | 10% hydroxylamine | 80 | 60 | 2776 | A |
| 25 | 100 mM LiOH | NH$_3$ 20% | 10% hydroxylamine | 80 | 60 | 2426 | A |
| 26 | 100 mM Diethylamine | NH$_3$ 20% | 10% hydroxylamine | 80 | 60 | 1871 | B |
| 27 | 80% sat. Ca(OH)$_2$ | NH$_3$ 20% | 10% hydroxylamine | 80 | 60 | 1234 | B |
| 28 | 80% sat. Ca(Cl)$_2$ | NH$_3$ 20% | 10% hydroxylamine | 80 | 60 | 1004 | B |
| 29 | 80% sat. Ba(OAc)$_2$ | NH$_3$ 20% | 10% hydroxylamine | 80 | 60 | 1641 | B |
| 30 | 80% sat. Mg(OAc)$_2$ | NH$_3$ 20% | 10% hydroxylamine | 80 | 60 | 389 | C |
| 31 | 80% sat. Sr(OH)$_2$ | NH$_3$ 20% | 10% hydroxylamine | 80 | 60 | 1287 | B |
| 32 | 80% sat. Sr(OAc)$_2$ | NH$_3$ 20% | 10% hydroxylamine | 80 | 60 | 1461 | B |
| 33 | 100 mM LiOH | — | 10% hydroxylamine | 80 | 60 | 1252 | B |
| 34 | 100 mM LiOH | Ethylenediamine 20% | 10% hydroxylamine | 80 | 60 | 1727 | B |
| 35 | 100 mM LiOH | Butylamine 20% | 10% hydroxylamine | 80 | 60 | 1031 | C |
| 36 | 100 mM LiOH | Ethanolamine 20% | 10% hydroxylamine | 80 | 60 | 1381 | B |
| 37 | 100 mM LiOH | Dimethylamine 10% | 10% hydroxylamine | 80 | 60 | 1473 | C |
| 38 | 100 mM LiOH | methylamine 8% | 10% hydroxylamine | 80 | 60 | 1473 | C |
| 39 | 100 mM LiOH | 100 mM DABCO | 10% hydroxylamine | 80 | 60 | 1957 | B |
| 40 | 100 mM LiOH | 100 mM Morpholine | 10% hydroxylamine | 80 | 60 | 1967 | B |
| 41 | 100 mM LiOH | 100 mM 2-Amidobenzamide | 10% hydroxylamine | 80 | 60 | 904 | C |

TABLE 1B

| Test Example | Basic reagent | Amines | Hydroxylamines | Temperature (° C.) | Time (min) | Yield | Results |
|---|---|---|---|---|---|---|---|
| 42 | 100 mM LiOH | 100 mM Anthranilic acid | 10% hydroxylamine | 80 | 60 | 21 | D |
| 43 | 2M KOH | NH$_3$ 7.5% | 10% hydroxylamine | 80 | 60 | 1525 | B |
| 44 | 1M KOH | NH$_3$ 7.5% | 10% hydroxylamine | 80 | 60 | 998 | C |
| 45 | 200 mM KOH | NH$_3$ 7.5% | 10% hydroxylamine | 80 | 60 | 835 | C |
| 46 | 50 mM KOH | NH$_3$ 7.5% | 10% hydroxylamine | 80 | 60 | 747 | C |
| 47 | 20 mM KOH | NH$_3$ 7.5% | 10% hydroxylamine | 80 | 60 | 874 | C |
| 48 | 2 mM KOH | NH$_3$ 7.5% | 10% hydroxylamine | 80 | 60 | 994 | C |
| 49 | 200 mM LiOH | 40 mM Morpholine | 10% hydroxylamine | 80 | 60 | 1773 | A |
| 50 | 200 mM DBU | 40 mM Morpholine | 10% hydroxylamine | 80 | 60 | 2669 | A |
| 51 | 200 mM DBU | 100 mM Morpholine | 10% hydroxylamine | 80 | 60 | 1449 | B |
| 52 | 200 mM DBU | 100 mM Morpholine | 5% hydroxylamine | 80 | 60 | 1150 | B |
| 53 | 200 mM DBU | 100 mM Morpholine | 3% hydroxylamine | 80 | 60 | 904 | C |
| 54 | 200 mM DBU | 100 mM Morpholine | 1% hydroxylamine | 80 | 60 | 875 | C |
| 55 | 200 mM DBU | 100 mM Morpholine | 10% hydroxylamine | 50 | 60 | 1837 | A |
| 56 | 200 mM DBU | 100 mM Morpholine | 10% hydroxylamine | 50 | 120 | 1707 | B |
| 57 | 200 mM DBU | 100 mM Morpholine | 10% hydroxylamine | 50 | 240 | 1217 | C |
| 58 | 200 mM DBU | 100 mM Morpholine | 10% hydroxylamine | RT | 60 | 37 | D |
| 59 | 200 mM DBU | 100 mM Morpholine | 10% hydroxylamine | RT | 180 | 103 | C |
| 60 | 200 mM DBU | 100 mM Morpholine | 10% hydroxylamine | RT | 360 | 174 | C |
| 61 | 200 mM DBU | 100 mM Morpholine | 10% hydroxylamine | RT | 960 | 1397 | B |
| 62 | 400 mM DBU | — | 200 mM hydroxylamine HCl | 80 | 60 | 55 | C |
| 63 | 400 mM LiOH | — | 200 mM hydroxylamine HCl | 80 | 60 | 5 | D |
| 64 | 200 mM DBU | NH$_3$ 19.2% | 10% hydroxylamine | 80 | 60 | 173 | C |
| 65 | 200 mM DBU | — | 10% hydroxylamine | 80 | 60 | 3580 | A |
| 66 | 200 mM TMG | — | 10% hydroxylamine | 80 | 60 | 3235 | A |

TABLE 1B-continued

| Test Example | Basic reagent | Amines | Hydroxylamines | Temperature (° C.) | Time (min) | Yield | Results |
|---|---|---|---|---|---|---|---|
| 67 | 200 mM t-butyl TMG | — | 10% hydroxylamine | 80 | 60 | 3331 | A |
| 68 | 600 mM DBU | 40 mM Morpholine | 10% hydroxylamine | 80 | 60 | 3424 | A |
| 69 | 200 mM DBU | 40 mM Morpholine | 10% hydroxylamine | 80 | 60 | 2894 | A |
| 70 | 100 mM DBU | 40 mM Morpholine | 10% hydroxylamine | 80 | 60 | 2902 | A |
| 71 | 60 mM DBU | 40 mM Morpholine | 10% hydroxylamine | 80 | 60 | 2093 | B |
| 72 | 200 mM DBU | NH$_3$ 15% | 10% hydroxylamine | 80 | 60 | 2740 | A |
| 73 | 200 mM TBD | — | 10% hydroxylamine | 80 | 60 | 2864 | A |
| 74 | 200 mM MTBD | — | 10% hydroxylamine | 80 | 60 | 3154 | A |
| 75 | 200 mM Proton sponge | — | 10% hydroxylamine | 80 | 60 | 53 | C |
| 76 | 600 mM DBU | — | 10% hydroxylamine | 80 | 60 | 2779 | A |
| 77 | 200 mM DBU | — | 10% hydroxylamine | 80 | 60 | 1688 | B |
| 78 | 100 mM DBU | — | 10% hydroxylamine | 80 | 60 | 2244 | A |
| 79 | 60 mM DBU | — | 10% hydroxylamine | 80 | 60 | 1846 | B |
| 80 | 4% cetyltrimethyl ammonium hydroxide | — | 10% hydroxylamine | 80 | 60 | 2235 | A |

(1) In Test Examples 1 and 2, the tests were performed in order to confirm the impact of a combination of lithium hydroxide and ammonia. As the result, the yield was significantly increased in Test Example 1 in which lithium hydroxide and ammonia were used in combination, compared to Test Example 2 in which ammonia was not added.

(2) In Test Examples 4 to 6, use of a calcium salt of an alkaline earth metal was compared to use of calcium hydroxide as a basic reagent. As the result, excellent results were obtained from both calcium compounds, and particularly the yield of calcium hydroxide was the highest. Further, compared to lithium hydroxide, the yield itself was decreased, but isomerization (epimerization) which is a kind of decomposition reaction was able to be suppressed.

(3) In Test Examples 8 to 14, the comparison was carried out by changing the concentration condition of hydroxylamines. As the result, effects were not able to be obtained in a case where 0.5% hydroxylamine having a concentration of 150 mM was used. Meanwhile, an effect for stabilizing sugar chains was able to be obtained in a case where 2% hydroxylamine having a concentration of 600 mM was used.

(4) In Test Examples 15 to 20, the comparison was carried out by changing the condition of the reaction time. As the result, the most preferable results were obtained under a temperature condition of 80° C. using ammonia and calcium acetate for a reaction time of 2 hours. However, it was found that decomposition of liberated sugar chains proceeds in a case where the reaction time exceeds 2 hours.

(5) In Test Examples 21 to 26, the comparison was carried out by changing the basic reagent (alkali catalyst). As the result, sugar chains were able to be liberated even with a weak alkali, and preferable yields and results were able to be obtained in each basic reagent.

(6) In Test Examples 27 to 32, the comparison was carried out using a salt or a hydroxide of an alkaline earth metal dissolved in various ammonia water of the basic reagents. As the result, excellent results were able to be obtained except for magnesium acetate.

(7) In Test Examples 33 to 38, the comparison was carried out by changing the amine. As the result, in a case of methylamine and dimethylamine, isomerization and decomposition (deamidation) of the amide were promoted while the yield was increased. In a case where ethylenediamine and ethanolamine were used, the yield was able to be increased while isomerization was suppressed.

(8) In Test Examples 39 to 42, the comparison was carried out using various amines having a low pKa. As the result, in a case where DABCO and morpholine were used, excellent yields and results were able to be obtained. Particularly, in a case where DABCO was used, deamidation was not found at all.

(9) In Test Examples 43 to 48, the comparison was performed by changing the concentration (2 mM to 2 M) of KOH. As the result, preferable results were able to be obtained in a case where the concentration of KOH was high.

(10) In Test Examples 49 and 50, DBU was used as the basic reagent and compared with lithium hydroxide. As the result, a more preferable yield was able to be obtained with DBU rather than lithium hydroxide.

(11) In Test Examples 51 to 54, the comparison was carried out by changing the concentration of hydroxylamines in the presence of DBU. As the result, preferable yields and results were able to be obtained in a concentration-dependent manner until the concentration of hydroxylamine reached at least 10%.

(12) In Test Examples 55 to 57, the comparison was carried out by changing the reaction time (60 minutes to 240 minutes) at 50° C. in the presence of DBU. As the result, 1 hour was most preferable. Further, in a case where the reaction time became 1 hour or longer, the yields and the results were worsen as the reaction time became longer.

(13) In Test Examples 58 to 61, the reaction times at room temperature were compared. As the result, the reaction rate was low at room temperature, and it took 16 hours to obtain approximately half the yield of the reaction using an enzyme.

(14) In Test Examples 62 and 63, the test results were compared based on the use of hydroxylamine hydrochloride as the hydroxylamines in DMSO and examined (in the table, DMSO was not noted). As the result, it was found that the reaction was unlikely to proceed in a case where DMSO was used as a solvent.

(15) In Test Examples 64 to 67, the test results were compared based on the use of various organic bases other than DBU. As the result, remarkably excellent yields and results were able to be obtained except for the case where DBU and ammonia were used in combination.

(16) In Test Examples 68 to 71, the comparison was carried out by changing the concentration of DBU. As the result, preferable yields and results were able to be obtained in a case where the concentration of DBU was high. Specifically, excellent effects were able to be obtained by using DBU having a concentration of 100 mM or greater.

(17) In Test Examples 72 to 75, the test results were compared based on the use of various organic bases other than DBU. As the result, preferable yields were not able to be obtained in a case where Proton sponge was used. On the contrary, preferable yields and results were able to be obtained in a case where organic bases other than Proton sponge were used.

(18) In Test Examples 76 to 79, the comparison was carried out by changing the concentration of DBU in the absence of amines. As the result, excellent effects were able to be obtained by using DBU having a concentration of 100 mM or greater.

(19) In Test Example 80, a 4% cetyltrimethylammonium hydroxide was examined. As the result, an excellent yield and excellent results were able to be obtained.

Example 8

<Reaction for Liberating O-Binding Sugar Chains Under Various Conditions>

In the reaction solution containing the hydroxylamines (a), the basic reagent (b), and/or the amines (c), various tests were performed by changing various conditions such as the type and the concentration of the reagent, the temperature, the reaction time, and the reaction time. The conditions and the yields in each test example are listed in Tables 2A and 2B. Further, 20 μg of bovine fetuin was used as the glycoprotein in Test Examples 1 to 52. Further, the concentration of each reagent indicates the final concentration, and the yield indicates the total area value of all sugar chain peaks in HPLC. In addition, the result "A" indicates that the yield of sugar chains was 2000 or greater and the amount of peeling products was 20% or less, the result "B" indicates that the amount of peeling products was 20% or greater or the yield of sugar chains was in a range of 1000 to 2000, the result "C" indicates that the yield of sugar chains was in a range of 200 to 1000, and the result "D" indicates that the yield of sugar chains was 200 or less.

TABLE 2A

| Test Example | Basic reagent | Amines | Hydroxylamines | Temperature (°C.) | Time (min) | Yield | Results |
|---|---|---|---|---|---|---|---|
| 1 | 100 mM LiOH | $NH_3$ 10.4% | 8.3% hydroxylamine | 45 | 960 | 2770 | B |
| 2 | 100 mM LiOH | $NH_3$ 10.4% | — | 45 | 960 | 454 | C |
| 3 | 40% Sat. $Ca(Oac)_2$ | $NH_3$ 10% | 20% hydroxylamine | 60 | 180 | 1541 | B |
| 4 | — | $NH_3$ 10% | 20% hydroxylamine | 60 | 180 | 619 | C |
| 5 | — | — | 33% hydroxylamine | 45 | 960 | poor | D |
| 6 | 600 mM NaOAc | — | 10% hydroxylamine | 45 | 960 | poor | D |
| 7 | — | 20% Dimethylamine | 10% hydroxylamine | 60 | 180 | 3351 | B |
| 8 | 100 mM $NaHCO_3$ | $NH_3$ 10% | 10% hydroxylamine | 60 | 180 | 1396 | B |
| 9 | 6 mM LiOH | $NH_3$ 8.75% | 10% hydroxylamine | 60 | 180 | 1124 | B |
| 10 | 300 mM LiOH | $NH_3$ 3.75% | 10% hydroxylamine | 60 | 5 | 1724 | B |
| 11 | 500 mM LiOH | $NH_3$ 10% | 10% hydroxylamine | 45 | 5 | 822 | C |
| 12 | 500 mM LiOH | $NH_3$ 10% | 10% hydroxylamine | 60 | 5 | 2483 | A |
| 13 | 500 mM LiOH | $NH_3$ 10% | 10% hydroxylamine | 75 | 5 | 3525 | A |
| 14 | 500 mM LiOH | $NH_3$ 10% | 10% hydroxylamine | 90 | 5 | 3453 | B |
| 15 | 500 mM LiOH | — | 10% hydroxylamine | 60 | 5 | 3222 | A |
| 16 | 500 mM LiOH | $NH_3$ 6.8% | 10% hydroxylamine | 60 | 5 | 3294 | A |
| 17 | 500 mM LiOH | $NH_3$ 3.4% | 10% hydroxylamine | 60 | 5 | 3108 | A |
| 18 | 250 mM LiOH | $NH_3$ 10% | 10% hydroxylamine | 60 | 5 | 3534 | A |
| 19 | 500 mM LiOH | — | — | 60 | 5 | 2691 | C |
| 20 | 500 mM LiOH | 164 mM Anthranilic acid | 10% hydroxylamine | 60 | 5 | 330 | C |
| 21 | 500 mM LiOH | — | 10% hydroxylamine | 60 | 5 | 2942 | A |
| 22 | 500 mM LiOH | 164 mM Anthranilic acid | 10% hydroxylamine | 60 | 5 | 1774 | B |
| 23 | 500 mM LiOH | 164 mM Anthranilic acid | 10% hydroxylamine | 60 | 10 | 2245 | A |
| 24 | 500 mM LiOH | 164 mM Anthranilic acid | 10% hydroxylamine | 60 | 30 | 2175 | A |
| 25 | 500 mM LiOH | 164 mM Anthranilic acid | 10% hydroxylamine | 60 | 60 | 2614 | B |
| 26 | 500 mM LiOH | 164 mM Anthranilic acid | 10% hydroxylamine | 60 | 120 | 1281 | B |
| 27 | 1.6M KOH | — | 10% hydroxylamine | 60 | 5 | poor | D |
| 28 | 1.6M KOH | 100 mM DABCO | 10% hydroxylamine | 60 | 5 | poor | D |
| 29 | 500 mM KOH | — | 10% hydroxylamine | 60 | 5 | 2187 | B |

TABLE 2B

| Test Example | Basic reagent | Amines | Hydroxylamines | Temperature (°C.) | Time (min) | Yield | Results |
|---|---|---|---|---|---|---|---|
| 30 | 500 mM NaOH | — | 10% hydroxylamine | 60 | 5 | 1853 | B |
| 31 | 500 mM LiOH | — | 10% hydroxylamine | 60 | 5 | 1799 | B |
| 32 | 500 mM LiOH | 100 mM DABCO | 10% hydroxylamine | 60 | 5 | 1305 | B |
| 33 | 200 mM DBU | — | 10% hydroxylamine | 60 | 5 | 2093 | A |
| 34 | 200 mM LiOH | — | 10% hydroxylamine | 60 | 5 | 1215 | B |
| 35 | 200 mM DBU | — | 10% hydroxylamine | RT | 20 | 140 | C |
| 36 | 200 mM DBU | — | 10% hydroxylamine | RT | 60 | 287 | C |
| 37 | 200 mM DBU | — | 10% hydroxylamine | RT | 120 | 352 | C |
| 38 | 200 mM DBU | — | 10% hydroxylamine | RT | 240 | 1095 | B |
| 39 | 200 mM DBU | 100 mM DABCO | 10% hydroxylamine | 60 | 5 | 1498 | B |

TABLE 2B-continued

| Test Example | Basic reagent | Amines | Hydroxylamines | Temperature (° C.) | Time (min) | Yield | Results |
|---|---|---|---|---|---|---|---|
| 40 | 200 mM TMG | — | 10% hydroxylamine | 60 | 10 | 1804 | A |
| 41 | 200 mM t-butyl TMG | — | 10% hydroxylamine | 60 | 10 | 971 | B |
| 42 | 200 mM TBD | — | 10% hydroxylamine | 60 | 10 | 1820 | B |
| 43 | 200 mM MTBD | — | 10% hydroxylamine | 60 | 10 | 1859 | B |
| 44 | 200 mM Proton sponge | — | 10% hydroxylamine | 60 | 10 | 338 | C |
| 45 | 200 mM DBU | — | 10% hydroxylamine | 60 | 10 | 1588 | B |
| 46 | 200 mM DBU | — | 10% hydroxylamine | 60 | 10 | 3278 | A |
| 47 | 600 mM DBU | — | 10% hydroxylamine | 60 | 10 | 4475 | A |
| 48 | 10% DBU (approximately 1.3M) | — | 20% hydroxylamine (6M) | 60 | 5 | 4143 | A |
| 49 | 10% DBU | — | 10% hydroxylamine | 60 | 5 | 3957 | A |
| 50 | 10% DBU | — | 5% hydroxylamine (1.5M) | 60 | 5 | 4290 | A |
| 51 | 10% DBU | — | 2% hydroxylamine (0.5M) | 60 | 5 | 4296 | A |
| 52 | 4% cetyltrimethyl ammonium hydroxide | — | 10% hydroxylamine | 60 | 5 | 3785 | A |

(1) In Test Examples 3 and 4, the test results were compared based on the presence or absence of calcium in a case where ammonia was used as a basic reagent. As the result, in a case where calcium was present, the yield was increased so that preferred results were able to be obtained.

(2) In Test Examples 5 and 6, the comparison was carried out without a base or using a base weaker than ammonia. As the result, it was found that the basicity stronger than that of ammonia is indispensable for liberating sugar chains.

(3) In Test Examples 7 to 10, the test results were compared based on a difference in strength of alkalis. As the result, preferable results were able to be obtained in all test examples. Further, the yield was increased under a strong alkaline condition.

(4) In Test Examples 11 to 14, the comparison was carried out by changing the temperature under a strong alkaline condition. As the result, the yield was increased with an increase of the temperature in a temperature range of 60° C. to 75° C., and remarkably excellent results were obtained. Meanwhile, preferable results were obtained even at a temperature of 90° C., but the yield was slightly decreased and peeling began to increase.

(5) In Test Examples 15 to 18, the comparison was carried out by changing the ammonia concentration in a strong alkaline condition. As the result, under the strong alkaline condition, the presence of ammonia was not necessary for liberation of O-binding sugar chains.

(6) In Test Example 19, the comparison was carried out based on the impact of the presence or absence of hydroxylamine. As the result, most of the sugar chains caused peeling under the condition of the absence of hydroxylamine.

(7) In Test Examples 20 to 26, the test results were compared based on the impact obtained by changing the reaction time in the presence of anthranilic acid. Further, DMSO was added to the reaction solution in Test Examples 21 to 26. As the result, DMSO was necessary in a case where anthranilic acid was added, and O-binding sugar chains were able to be liberated while peeling was suppressed during the reaction time of 30 minutes under the conditions of the test examples. Meanwhile, peeling occurred in a case where the reaction time was 30 minutes or longer, and decomposed matter different from peeling was generated in a case where the reaction time was 1 hour or longer.

(8) In Test Examples 27 and 28, use of KOH having a high concentration was examined in place of LiOH. As the result, O-binding sugar chains were not able to be liberated at all in a case where KOH having a high concentration was used.

(9) In Test Examples 29 and 30, alkalis (KOH and NaOH) were examined. As the result, the amount of disialyl sugar chains as liberated O-binding sugar chains was small in both alkalis, and the results obtained using LiOH were preferable.

(10) In Test Examples 31 and 32, the effects of DABCO were examined. As the results, the yield was decreased in a case where DABCO was added, but the peeling was able to be suppressed.

(11) In Test Examples 33 and 34, DBU serving as a basic reagent was compared to LiOH serving as a basic reagent. As the result, in a case where DBU was used during the test, the yield was excellent and the amount of disialyl sugar chains was relatively large.

(12) In Test Examples 35 to 38, the test results were compared based on the length of reaction time in a case where 200 mM DBU and 10% hydroxylamine were used. As the result, the reaction for liberating O-binding sugar chains proceeded over time even at room temperature. Further, peeled sugar chains were hardly found even after the reaction carried out for 4 hours.

(13) In Test Examples 40 to 44, use of other organic bases was examined. As the result, O-binding sugar chains such as TMG, t-butyl TMG, TBD, and MTBD were all able to be liberated. Particularly in a case of TMD, TBD, and MTBD, more preferable yields and results were able to be obtained.

(14) In Test Examples 45 to 47, the concentration of DBU was examined. As the result, the yield was increased in a case where the concentration of DBU became higher.

(15) In Test Examples 48 to 51, the concentration of hydroxylamine was examined. As the result, peeling was able to be suppressed in a case where the amount of hydroxylamine was relatively higher than the amount of DBU.

(16) In Test Example 52, test results were obtained by using a 4% cetyltrimethylammonium hydroxide as a basic reagent. An excellent yield and excellent results were able to be obtained.

Example 9

<Analysis of O-Binding Sugar Chains from Bovine Fetuin Combined with Reagent Removal Using Monolith Silica>
(Reaction for Liberating O-Binding Sugar Chains Using 50% Hydroxylamine)

Bovine fetuin (20 μg) was dissolved in 50 μL of 50% hydroxylamine, and 10 μL of 1,8-diazabicyclo[5.4.0]undec-7-ene (DBU) was added thereto, and the solution was mixed and heated at 60° C. for 20 minutes using a heat block during draft. Thereafter, the reaction solution was immediately cooled in an ice bath and then neutralized with 1 N hydrochloric acid.

(Recovery of Sugar Chains Liberated by Reaction Using 50% Hydroxylamine)

200 µL of acetone or 200 µL of salicylaldehyde was added to the neutralized reaction solution and the reaction solution was stirred. Further, 16 mL of acetonitrile was added to the reaction solution, the total amount of the reaction solution was applied to monolith silica (silica monolith spin column, Cleanup column, manufactured by Sumitomo Bakelite Co., Ltd.) equilibrated with acetonitrile in advance, and the monolith silica washed with 1.2 mL of acetonitrile. Next, sugar chains were eluted from the monolith silica using 100 µL of 10% acetic acid, mixed with 900 µL of pure water, and subjected to a desalting treatment using a graphite carbon cartridge in the same manner as in Example 1, and sugar chains were eluted using 1 mL of 50% acetonitrile containing 0.1% trifluoroacetic acid (TFA) and dried under reduced pressure.

(Analysis of Liberated Sugar Chains)

The dried sugar chains were dissolved in 25 µL of 10% acetic acid, and the sugar chains were subjected to fluorescent labeling using picoline borane and 2-aminobenzoic acid. The fluorescent-labeled sugar chains were analyzed according to HPLC after an excess amount of the reagent was removed using monolith silica (silica monolith spin column, Cleanup column, manufactured by Sumitomo Bakelite Co., Ltd.).

Example 10

<Reaction for Liberating O-Binding Sugar Chains Using 10% Hydroxylamine>

Bovine fetuin (20 µg) was dissolved in 50 µL of 10% hydroxylamine, and 10 µL of DBU was added thereto, and the solution was mixed and heated at 60° C. for 20 minutes using a heat block during draft. Thereafter, the reaction solution was immediately cooled in an ice bath and then neutralized with 1 N hydrochloric acid.

(Recovery of Liberated Sugar Chains)

The neutralized reaction solution was subjected to a desalting treatment using a solid phase extraction cartridge (HyperSep Hypercarb, 25 mg, manufactured by Thermo Fisher Scientific, Inc.) filled with graphite carbon in the same manner as in Example 1, and sugar chains were eluted using 1 mL of 50% acetonitrile containing 0.1% TFA and dried under reduced pressure.

(Analysis of Liberated Sugar Chains)

The sugar chains were subjected to fluorescent labeling in the same manner as in Example 9 and analyzed according to HPLC.

Example 11

<Reaction for Liberating O-Binding Sugar Chains Using 50% Hydroxylamine>

Bovine fetuin (20 µg) was dissolved in 50 µL of 50% hydroxylamine, and 10 µL of DBU was added thereto, and the solution was mixed and heated at 60° C. for 20 minutes using a heat block during draft. Thereafter, the reaction solution was immediately cooled in an ice bath and then neutralized with 1 N hydrochloric acid.

(Recovery of Liberated Sugar Chains)

The neutralized reaction solution was subjected to a desalting treatment using a solid phase extraction cartridge (HyperSep Hypercarb, 25 mg, manufactured by Thermo Fisher Scientific, Inc.) filled with graphite carbon in the same manner as in Example 1, and sugar chains were eluted using 1 mL of 50% acetonitrile containing 0.1% TFA and dried under reduced pressure.

(Analysis of Liberated Sugar Chains)

The sugar chains were subjected to fluorescent labeling in the same manner as in Example 9 and analyzed according to HPLC.

Figure 8:
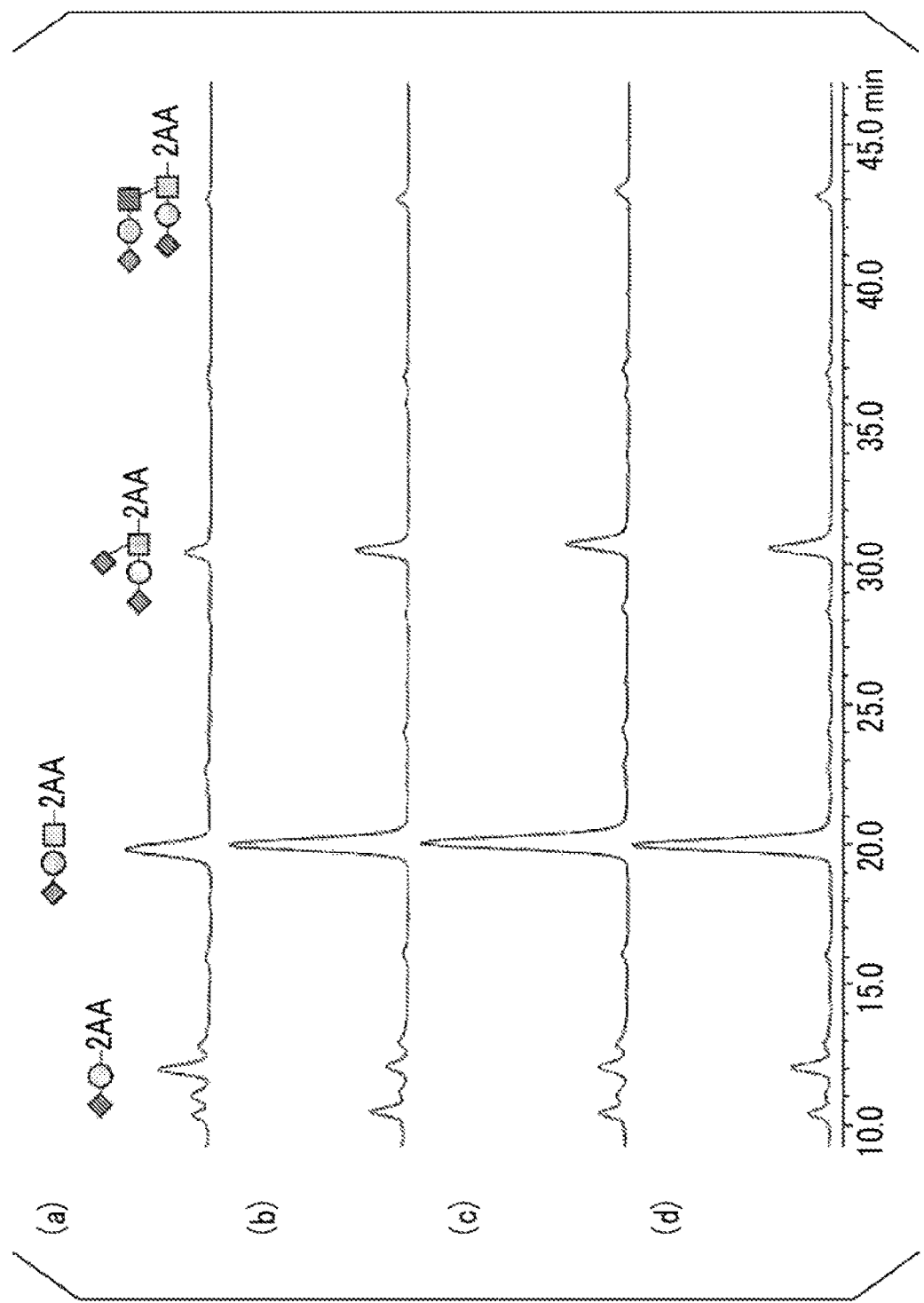
FIG. 8 shows an HPLC chromatogram of O-binding sugar chains liberated from bovine fetuin in Examples 9 to 11 through (a) to (d). The result of Example 10 is shown in (a), the result of Example 11 is shown in (b), the result of Example 9 (acetone treatment) is shown in (c), and the result of Example 9 (salicylaldehyde treatment) is shown in (d).

In FIG. 8, (a) to (d) each show the chromatogram showing the results obtained by analyzing, according to HPLC, the sugar chains subjected to fluorescent labeling in Examples 9 to 11. In (a) to (d) of FIG. 8, the horizontal axis shows the elution time and the vertical axis shows the fluorescence intensity (relative value).

Further, (a) of FIG. 8 shows the results of Example 10, (b) of FIG. 8 shows the results of Example 11, (c) of FIG. 8 shows the results of Example 9 (acetone treatment), and (d) of FIG. 8 shows the results of Example 9 (salicylaldehyde treatment). As the results, it was clarified that peeling was suppressed by using hydroxylamine at a concentration of 50% and performing a purification treatment using monolith silica after performing an acetone or salicylaldehyde treatment, and the sugar chains were able to be analyzed with high yields.

Example 12

<Examination of Method for Recovering Sugar Chains from Monolith Silica>

(Reaction for Liberating O-Binding Sugar Chains Using 50% Hydroxylamine)

Bovine fetuin (20 µg) was dissolved in 50 µL of 50% hydroxylamine, and 10 µL of DBU was added thereto, and the solution was mixed and heated at 60° C. for 20 minutes using a heat block during draft. Thereafter, the reaction solution was immediately cooled in an ice bath and then neutralized with 1 N hydrochloric acid.

(Recovery of Sugar Chains Liberated by Reaction Using 50% Hydroxylamine)

200 µL of acetone was added to the neutralized reaction solution and the reaction solution was stirred. Further, 20 mL of acetonitrile was added to the reaction solution, the total amount of the reaction solution was applied to monolith silica (silica monolith spin column, Cleanup column, manufactured by Sumitomo Bakelite Co., Ltd.) equilibrated with acetonitrile in advance, and the monolith silica washed with 1.2 mL of acetonitrile.

(Recovery and Analysis of Sugar Chains)

Next, 25 µL of 10 acetic acid was added to monolith silica, and the solution was recovered. Further, 25 µL of a mixed solution of picoline borane and 2-aminobenzoic acid was added to the monolith silica, the solution was recovered and mixed with the above-described solution for the reaction at 50° C. for 3 hours, and sugar chains was subjected to fluorescent labeling. The fluorescent-labeled sugar chains were analyzed according to HPLC after an excess amount of the reagent was removed using monolith silica (silica monolith spin column, Cleanup column, manufactured by Sumitomo Bakelite Co., Ltd.).

Figure 9:
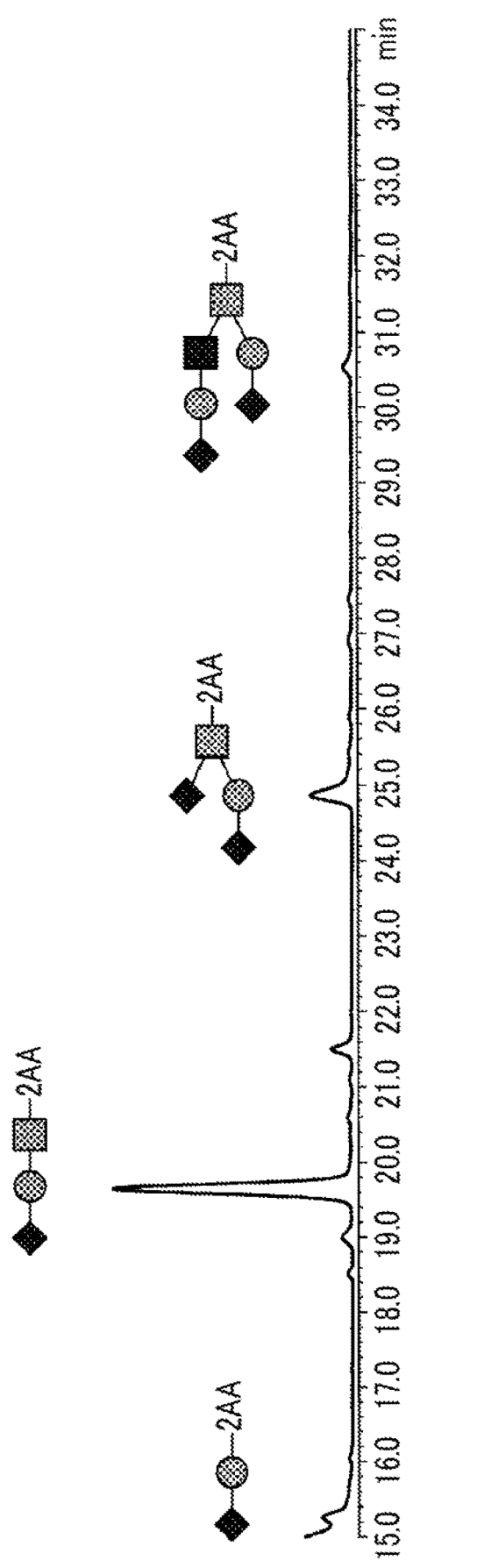
FIG. 9 shows an HPLC chromatogram of O-binding sugar chains liberated from bovine fetuin in Example 12.

FIG. 9 is a chromatogram showing the results obtained by analyzing, according to HPLC, the sugar chains subjected to fluorescent labeling in Example 12. In FIG. 9, the horizontal axis shows the elution time and the vertical axis shows the fluorescence intensity (relative value). As the result, it confirmed that the target sugar chain peaks were obtained even in a case where the method for recovering sugar chains was changed.

INDUSTRIAL APPLICABILITY

According to the method of the present invention, it is possible to liberate sugar chains from a glycoprotein in a short treatment time while suppressing decomposition of the sugar chains by using safe and inexpensive drugs and to recover the liberated sugar chains as a mixture containing a sugar chain oxime.

REFERENCE SIGNS LIST

100: device
110: glycoprotein
120, 170: container
130: container holding portion
140: reagent introduction unit
141: introduction unit (reaction solution introduction unit, ketone introduction unit, aldehyde introduction unit, acid anhydride introduction unit, labeling reagent introduction unit)
142, 143, 144: liquid supply tube
145, 146, 147: valve
150: tank
151: reaction solution
152: ketone, aldehyde, acid anhydride
153: labeling reagent
160: solid phase holding portion
171: solid phase
180: solid-liquid separation unit
181: rack
182: drive shaft
183: motor
190: container transfer unit
195: temperature adjusting unit

The invention claimed is:

1. A method for liberating sugar chains from a glycoprotein having proteins and at least one of N-binding sugar chains and O-binding sugar chains, the at least one of N-binding sugar chains and O-binding sugar chains being bound to the proteins through an N-glycosidic bond or an O-glycosidic bond, respectively, the method comprising:
a step of bringing a reaction solution which contains hydroxylamines (a) and a basic reagent (b) into contact with the glycoprotein and cleaving the N-glycosidic bond or the O-glycosidic bond, to obtain a mixed solution of the sugar chains liberated from the glycoprotein and the reaction solution,
wherein, in the step of bringing the reaction solution into contact with the glycoprotein, a pH of the reaction solution is in a range of 8 to 14.

2. The method according to claim 1,
wherein the reaction solution contains 2% to 70% (w/w) of the hydroxylamines (a).

3. The method according to claim 1,
wherein the reaction solution further contains amines (c), and
wherein the amines (c) are at least one compound selected from the group consisting of ammonia water, a methylamine aqueous solution, a dimethylamine aqueous solution, ethylamine, diethylamine, ethanolamine, ethylenediamine, butylamine, morpholine, DABCO, and anthranilic acid.

4. The method according to claim 1,
wherein the sugar chains liberated from the glycoprotein contain a sugar chain oxime.

5. The method according to claim 1,
wherein the hydroxylamines (a) are at least one compound selected from the group consisting of hydroxylamine, a salt of hydroxylamine, O-substituted hydroxylamine, and a salt of O-substituted hydroxylamine.

6. The method according to claim 1,
wherein the basic reagent (b) is at least one selected from the group consisting of a hydroxide of an alkali metal, a weak acid salt of an alkali metal, a hydroxide of an alkaline earth metal, a salt of an alkaline earth metal dissolved in an ammonia aqueous solution, and an organic base.

7. The method according to claim 6,
wherein the hydroxide of an alkali metal is lithium hydroxide, sodium hydroxide, or potassium hydroxide,
the weak acid salt of an alkali metal is sodium bicarbonate or sodium carbonate,
the hydroxide of an alkaline earth metal is calcium hydroxide, barium hydroxide, or strontium hydroxide,
the salt of an alkaline earth metal is calcium acetate, calcium chloride, barium acetate, or magnesium acetate, and
the organic base is 1,8-diazabicyclo[5.4.0]undec-7-ene, 1,5,7-triazabicyclo[4.4.0]dec-5-ene, 7-methyl-1,5,7-triazabicyclo[4.4.0]dec-5-ene, 1,1,3,3-tetramethylguanidine, 2-tert-butyl-1,1,3,3-tetramethylguanidine, or cetyltrimethylammonium hydroxide.

8. The method according to claim 1, further comprising:
a step of adding a ketone, an aldehyde, or an acid anhydride to the mixed solution and converting the hydroxylamines (a) remaining in the mixed solution to a ketoxime, an aldoxime, or an amide;
a step of bringing the mixed solution into contact with a solid phase having an affinity for sugar chains so that the sugar chains liberated from the glycoprotein are adsorbed on the solid phase; and
a step of eluting the sugar chains from the solid phase.

9. A method for analyzing sugar chains of a glycoprotein, comprising:
a step of liberating sugar chains from a glycoprotein using the method according to claim 1;
a step of labeling the liberated sugar chains, which includes labeling of a sugar chain oxime; and
a step of analyzing the labelled sugar chain.

10. A method for analyzing sugar chains of a glycoprotein, comprising:
a step of liberating sugar chains from a glycoprotein using the method according to claim 1; and
a step of fluorescent labeling the liberated sugar chains, which includes labeling of a sugar chain oxime.

11. The method according to claim 1,
wherein the hydroxylamines (a) are at least one compound selected from a hydroxylamine aqueous solution, hydroxylamine sulfate, hydroxylamine phosphate, O-methylhydroxylamine hydrochloride, O-methylhydroxylamine hydrochloride, O-ethylhydroxylamine hydrochloride, O-(tetrahydro-2H-pyran-2-yl)hydroxylamine, nitrobenzylhydroxylamine hydrochloride, O-tert-butyldimethylsilylhydroxylamine, and O-trimethylsilylhydroxylamine.

* * * * *